US012115155B2

(12) United States Patent
Nielsen et al.

(10) Patent No.: US 12,115,155 B2
(45) Date of Patent: *Oct. 15, 2024

(54) SOLID DOSAGE FORM OF A NICOTINE CONCENTRATION

(71) Applicant: Fertin Pharma A/S, Vejle (DK)

(72) Inventors: Bruno Provstgaard Nielsen, Vejle Øst (DK); Kent Albin Nielsen, Brande (DK)

(73) Assignee: Fertin Pharma A/S, Vejle (DK)

( * ) Notice: Subject to any disclaimer, the term of this patent is extended or adjusted under 35 U.S.C. 154(b) by 974 days.

This patent is subject to a terminal disclaimer.

(21) Appl. No.: 16/770,345

(22) PCT Filed: Dec. 7, 2018

(86) PCT No.: PCT/DK2018/050338
§ 371 (c)(1),
(2) Date: Jun. 5, 2020

(87) PCT Pub. No.: WO2019/110075
PCT Pub. Date: Jun. 13, 2019

(65) Prior Publication Data
US 2023/0158011 A1 May 25, 2023

(30) Foreign Application Priority Data
Dec. 8, 2017 (DK) .................. PA 2017 70928

(51) Int. Cl.
*A61K 31/465* (2006.01)
*A61K 9/00* (2006.01)
*A61K 9/14* (2006.01)
*A61K 47/32* (2006.01)

(52) U.S. Cl.
CPC .......... *A61K 31/465* (2013.01); *A61K 9/0053* (2013.01); *A61K 9/146* (2013.01); *A61K 47/32* (2013.01)

(58) Field of Classification Search
CPC .................................................. A61K 9/0053
See application file for complete search history.

(56) References Cited

U.S. PATENT DOCUMENTS

| | | | |
|---|---|---|---|
| 4,866,046 A | 9/1989 | Amer | |
| 5,662,920 A * | 9/1997 | Santus | A61P 25/32 424/440 |
| 5,810,018 A | 9/1998 | Monte | |
| 5,935,604 A | 8/1999 | Illum | |
| 7,387,788 B1 | 6/2008 | Carrara et al. | |
| 8,529,939 B2 | 9/2013 | Masters et al. | |
| 8,597,679 B2 * | 12/2013 | Kolter | A61K 31/00 424/501 |
| 2001/0016593 A1 | 8/2001 | Wilhelmsen | |
| 2002/0002189 A1 | 1/2002 | Smith et al. | |
| 2006/0057207 A1 * | 3/2006 | Ziegler | A61K 9/2866 424/484 |
| 2007/0269386 A1 | 11/2007 | Steen et al. | |
| 2008/0286341 A1 | 11/2008 | Andersson et al. | |
| 2010/0108059 A1 | 5/2010 | Axelsson et al. | |
| 2010/0178353 A1 | 7/2010 | Mezaache et al. | |
| 2011/0206621 A1 | 8/2011 | Agarwal et al. | |
| 2011/0274628 A1 | 11/2011 | Borschke | |
| 2013/0177646 A1 | 7/2013 | Hugerth et al. | |
| 2013/0289079 A1 | 10/2013 | Chen | |
| 2014/0328973 A1 | 11/2014 | Nielsen | |
| 2015/0080442 A1 | 3/2015 | McCarty | |
| 2015/0096576 A1 | 4/2015 | Gao et al. | |
| 2017/0165252 A1 | 6/2017 | Mua et al. | |
| 2017/0172995 A1 * | 6/2017 | Repaka | A61K 31/465 |
| 2017/0189388 A1 | 7/2017 | Arnold | |
| 2019/0160019 A1 | 5/2019 | Nielsen | |
| 2019/0174812 A1 | 6/2019 | Nielsen et al. | |
| 2019/0175581 A1 | 6/2019 | Nielsen et al. | |
| 2020/0397691 A1 | 12/2020 | Nielsen et al. | |
| 2021/0345656 A1 | 11/2021 | Nielsen et al. | |

FOREIGN PATENT DOCUMENTS

| | | | | |
|---|---|---|---|---|
| CA | 2831715 A1 * | 10/2012 | ............. | A24B 15/16 |
| EP | 1366759 A1 | 12/2003 | | |
| EP | 2177213 A1 | 4/2010 | | |
| EP | 2446881 A1 | 5/2012 | | |
| JP | 2006518761 A | 8/2006 | | |
| JP | 2010526876 A | 8/2010 | | |
| JP | 2011519862 A | 7/2011 | | |
| JP | 2012505878 A | 3/2012 | | |
| JP | 2014503539 A | 2/2014 | | |
| JP | 2015-503581 A | 2/2015 | | |

(Continued)

OTHER PUBLICATIONS

International Search Report and Written Opinion dated Mar. 14, 2019 in International Application No. PCT/DK2018/050338, 12 pages.
International Search Report and Written Opinion dated Mar. 14, 2019 in International Application No. PCT/DK2018/050339, 12 pages.
International Search Report and Written Opinion dated May 13, 2019 in International Application No. PCT/DK2018/050337, 15 pages.
Laffleur, et al., "Comprehensive mucoadhesive study of anionic polymers and their derivative", European Polymer Journal, vol. 93, Aug. 2017, pp. 314-322.
U.S. Appl. No. 16/213,641, filed Dec. 7, 2018, US 2019-0175581A1, Pending.
U.S. Appl. No. 16/213,678, filed Dec. 7, 2018, US 2019-0174812 A1, Pending.
U.S. Appl. No. 16/770,313, filed Jun. 5, 2020, Pending.
U.S. Appl. No. 16/770,345, filed Jun. 5, 2020, Pending.
U.S. Appl. No. 16/770,375, filed Jun. 5, 2020, Pending.

(Continued)

Primary Examiner — Gina C Justice
(74) Attorney, Agent, or Firm — Lee & Hayes, P.C.

(57) ABSTRACT

The invention relates to an oral nicotine formulation for use in the alleviation of nicotine craving, the formulation comprising a content of nicotine and a content of a pH regulating agent, wherein the formulation provides a peak saliva concentration of nicotine of more than 0.3 mg/mL and a peak saliva pH of more than 7.5 during the first 120 seconds upon oral administration.

21 Claims, No Drawings

(56) References Cited

FOREIGN PATENT DOCUMENTS

| RU | 2153338 C2 | 7/2000 |
| --- | --- | --- |
| RU | 2608902 C2 | 1/2017 |
| TW | 201318650 A1 | 5/2013 |
| WO | WO2002085119 A1 | 10/2002 |
| WO | WO03055486 A1 | 7/2003 |
| WO | WO2003055486 A1 | 7/2003 |
| WO | WO2004075877 A1 | 9/2004 |
| WO | WO2007133140 A1 | 11/2007 |
| WO | WO2008037470 A1 | 4/2008 |
| WO | WO2008082808 A1 | 7/2008 |
| WO | WO2008140371 A1 | 11/2008 |
| WO | WO2008140372 A1 | 11/2008 |
| WO | WO2009007771 A1 | 1/2009 |
| WO | WO2009134947 A1 | 11/2009 |
| WO | WO2010044736 A1 | 4/2010 |
| WO | WO2012085043 A2 | 6/2012 |
| WO | WO2012134380 A1 | 10/2012 |
| WO | WO2013091631 A1 | 6/2013 |
| WO | WO2013103318 A1 | 7/2013 |
| WO | WO2019110072 A1 | 6/2019 |
| WO | WO2019110073 A1 | 6/2019 |

OTHER PUBLICATIONS

Russian Office Action mailed Dec. 17, 2021 in Russian Application No. 2020122405/04(038512), a foreign corresponding application of U.S. Appl. No. 16/213,641, 5 pages.

"Crospovidone ED". Nov. 2002. In: Rowe RC, Sheskey PJ, Weller PJ, eds. Handbook of Pharmaceutical Excipients, Pharmaceutical Press, London, UK, p. 184, XP002719370. 2 pages.

European Office Action dated Mar. 3, 2021 in European Application No. 18821992.7, a foreign corresponding application of U.S. Appl. No. 16/213,641, 8 pages.

European Office Action dated Mar. 3, 2021 in European Application No. 18821993.5, a foreign corresponding application of U.S. Appl. No. 16/213,678, 9 pages.

Hickman, "Melt in the Mouth," Nov. 2017, The Medicine Maker, Discovery and Development, downloaded Jan. 14, 2023 from https://themedicinemaker.com/discovery-development/melt-in-the-mouth, 9 pages.

Japanese Office Action dated Nov. 29, 2022 in Japanese Application No. JP2020-529346, a foreign corresponding application of U.S. Appl. No. 16/213,641, 8 pages.

"Cellulose, Microcrystalline," 2006. Eds. Rowe et al. In Handbook of Pharmaceutical Excipients, Fifth Edition, Pharmaceutical Press. London, England. pp. 132-135, 26 pages.

Conway, "Solid Dosage Forms", Mar. 2008. Ed. S. Cox In Pharmaceutical Manufacturing Handbook, Production and Processes, Chapter 4.1.11: Excerpt pp. 259-263.

"Crospovidone," 2006. Eds. Rowe et al. In Handbook of Pharmaceutical Excipients, Fifth Edition, Pharmaceutical Press. London, England. pp. 214-216, 26 pages.

Davies, "Oral Solid Dosage Forms," 2009. Ed. M. Gibson In Pharmaceutical Preformulation and Formulation, A Practical Guide from Candidate Drug Selection to Commercial Dosage Form, Second Edition, Chapter 11: Excerpt: pp. 397-399, 18 pages.

Deshmukh, "Mouth Dissolving Drug Delivery System: A Review," Jan. 2012. International Journal of PharmTech Research, 14(1): 412-421.

Dey et al., "Orodispersible tablets: A trend in drug delivery," Jul. 2010. Journal of Natural Science, Biology and Medicine, 1(1): 1-5.

Notice of Oppisition mailed May 11, 2022 in European Application No. 18821992.7, a foreign corresponding Application of U.S. Appl. No. 16/213,641, 3 pages.

"Guidance for Industry Oral Disintegrating Tablets," Dec. 2008. U.S. Department of Health and Human Services Food and Drug Administration Center for Drug Evaluation and Research, 6 pages.

"Kollidon® CL, Kollidon® CL-F, Kollidon® CL-SF, Kollidon® CL-M: Super-disintegrants and dissolution enhancers". Brochure from BASF The Chemical Company. www.pharma-solutions.basf.com, downloaded at least by May 11, 2022. 18 pages.

"Ludiflash® The taste of sucess: Making tablets as smooth as ice cream". Brochure from BASF The Chemical Company. www.pharma-ingredients.basf.com, downloaded at least by May 11, 2022. 12 pages.

Patil et al., "A Review on Mouth Dissolving Tablet," 2017. Journal of Applied Pharmaceutical Research, 5(2): 9-15.

Shahab et al., "Novel Delivery Systems for Nicotine Replacement Therapy as an Aid to Smoking Cessation and for Harm Reduction: Rationale, and Evidence for Advantages over Existing Systems," CNS Drugs (2013) 27:1007-1019.

Tillotson, "Comparison of Directly Compressible Drug Delivery Systems for Orally Disintegrating Tablets," 2014. SPI Pharma, 2 pages.

"Mannitol," 2006. Eds. Rowe et al. In Handbook of Pharmaceutical Excipients, Fifth Edition, Pharmaceutical Press. London, England. pp. 449-454, 28 pages.

Russian Search Report dated Jan. 15, 2024 in Russian Application No. 2022129278/04(064158), 2 pages.

European Search Report dated Sep. 14, 2021 in European Application No. 21182000.6, a foreign corresponding application of U.S. Appl. No. 16/213,641, 12 pages.

European Oral Summons dated Sep. 6, 2021 in European Application No. 18821993.5, a foreign corresponding application of U.S. Appl. No. 16/213,678, 17 pages.

"Mannitol" Jan. 2006. In: Rowe RC, Sheskey PJ, Weller PJ, eds. Handbook of Pharmaceutical Excipients, Pharmaceutical Press, London, UK, pp. 449-453, XP002537758 5 pages.

* cited by examiner

SOLID DOSAGE FORM OF A NICOTINE CONCENTRATION

CROSS REFERENCE TO RELATED APPLICATIONS

This application is a U.S. National Phase Application of International Application No. PCT/DK2018/050338, filed Dec. 7, 2018, which claims priority to Danish Application No. PA 2017 70928 filed Dec. 8, 2017, which are hereby incorporated by reference in their entirety.

FIELD OF INVENTION

The invention relates to oral nicotine formulations according to claim 1 and a method of using the same.

BACKGROUND

Different types of nicotine delivery vehicles have been applied for nicotine delivery to a user's mouth.

Such delivery vehicles include e.g. chewing gum tablets and mouth sprays.

The aim of obtaining a delivery vehicle facilitating alleviation of nicotine craving in the same way as a cigarette is however far from being reached.

In particular, it is noted that burning is restricting the prior art delivery vehicle's ability in delivering the required nicotine.

Moreover, obviously, the limited surface area of the oral mucosa compared to the lung severely limits the transfer of nicotine into the bloodstream.

SUMMARY

The invention relates to an oral nicotine formulation for use in the alleviation of nicotine craving, the formulation comprising a content of nicotine and a content of a pH regulating agent, wherein the formulation provides a peak saliva concentration of nicotine of more than 0.3 mg/mL and a peak saliva pH of more than 7.5 during the first 120 seconds upon oral administration.

An advantage of the invention may be that a high nicotine concentration in the oral cavity may be obtained. Particularly, the high nicotine concentration is provided with a correspondingly high pH value facilitating a high uptake of nicotine. This facilitates a high nicotine uptake, while leading to a surprisingly low level of burning in the throat.

Particularly, an advantage of the invention may be that the peak saliva concentration of nicotine and the peak saliva pH is obtained within the first 120 second upon oral administration. While the peak saliva concentration of nicotine and the peak saliva pH may in some embodiments be obtained almost immediately upon oral administration, some time, but not more than 120 second, may pass in other embodiments. This may depend of the delivery vehicle. For example, liquid nicotine mouth spray formulations may be used, where the peak saliva concentration of nicotine and the peak saliva pH may very fast, whereas for orally disintegrating tablets the time before the peak values depend on the disintegration.

Thus, an advantage of the invention may be that effective nicotine delivery may be combined with low burning levels in the throat.

A further advantage of the invention may be that by obtaining a relatively high peak saliva concentration of nicotine, an increased, but potentially only moderately increased, peak saliva pH may still obtain a very high nicotine uptake. Conventionally, a relatively high pH in the oral cavity is used to obtain the desired high uptake of nicotine. However, this may not be necessary within the scope of the present invention.

Contrary to expectations, experiments have shown that the permeability of nicotine across the buccal mucosa decreases relatively little when increasing the concentration of nicotine. For example, experiments have shown that an increase in the concentration of nicotine from 100 microgram/mL to 14,000 microgram/mL results in a decrease of about a factor of two. This is highly surprising and is utilized by aiming for concentrations of nicotine in the oral cavity, which are much higher than previously seen or desired. The present delivery vehicle thus benefits and aims for very high nicotine content in the oral cavity, thereby increasing the nicotine uptake. Furthermore, it has been realized that the effect of nicotine concentrations is thus at least comparable to the effect of pH regulation in the oral cavity. This is contrary to any expectations.

In the present context, it should be understood that said use in the alleviation of nicotine craving involves administering said oral nicotine formulation orally.

Thus, according to the invention, the formulation comprises a content of nicotine and a content of a pH regulating agent, wherein the formulation provides:

a peak saliva concentration of nicotine of more than 0.3 mg/mL and no more than 0.5 mg/mL and a peak saliva pH of more than 7.5 during the first 120 seconds upon oral administration, or a peak saliva concentration more than 0.5 mg/mL and a peak saliva pH of more than 7.5 during the first 120 seconds upon oral administration.

In an embodiment of the invention, the oral nicotine formulation comprises nicotine in an amount of at least 0.5 mg.

The amount of nicotine content is generally given in amount per dosage unless otherwise specified. If the dosage is in the form of a tablet, the amount will refer to the complete tablet. If the dosage is referred to a mouth spray the amount will refer to the weight of the referred substance in the instructed dose, e.g. the amount of substance referred to in relation to a single spray or e.g. the amount of substance in the instructed number of sprays related to the instructed timing.

According to an embodiment of the invention the oral nicotine formulation comprises nicotine in an amount of between 0.5 and 4.0 mg.

According to an embodiment of the invention the oral nicotine formulation comprises nicotine in an amount of at least 0.5 mg per dosage.

In an embodiment of the invention, the formulation provides a peak saliva concentration of nicotine of more than 0.4 mg/mL during the first 120 seconds upon oral administration.

In an embodiment of the invention, the formulation provides a peak saliva concentration of nicotine of more than 0.5 mg/mL during the first 120 seconds upon oral administration.

In an embodiment of the invention, the formulation provides a peak saliva concentration of nicotine of more than 0.3 mg/mL and no more than 0.5 mg/mL during the first 120 seconds upon oral administration.

In an embodiment of the invention, the oral nicotine formulation provides a peak saliva concentration of nicotine of more than 1.0 mg/mL during the first 120 seconds upon oral administration.

In embodiments where the formulation provides a peak saliva concentration of nicotine of more than 1.0 mg/mL during the first 120 seconds upon oral administration, the amount of nicotine in the tablet should be adjusted to at least the amount necessary for obtaining this. Depending on the specific formulation, the amount of nicotine in the tablet may be higher than 0.5 mg in some embodiments, such as e.g. at least 2 mg or at least 4.0 mg.

In an embodiment of the invention, the oral nicotine formulation provides a peak saliva concentration of nicotine of between 0.5 and 2.0 mg/mL during the first 120 seconds upon oral administration.

In an embodiment of the invention, the oral nicotine formulation comprises said pH regulating agent in an amount of at least 0.5% by weight of the formulation.

According to an embodiment of the invention, said content of pH regulating agent is between 0.5 and 5.0% by weight said formulation. This may especially be the case when the formulation is provided as a liquid mouth spray formulation.

According to an embodiment of the invention, said content of pH regulating agent is at least 2.7% by weight of said formulation.

According to an embodiment of the invention, said content of pH regulating agent is between 2.7 and 5.7% by weight said formulation. This may especially be the case when the formulation is provided as a solid formulation, such as an orally disintegrating tablet.

In an embodiment of the invention the pH regulating agent is selected from the list of carbonates, including monocarbonate, bicarbonate and sesquicarbonate, glycerinate, phosphate, glycerophosphate, acetate, glyconate or citrate of an alkali metal, ammonium, tris buffer, amino acids and mixtures thereof.

In an embodiment of the invention, the formulation provides a peak saliva pH of more than 8.0 during the first 120 seconds upon oral administration.

According to an embodiment of the invention the formulation provides a peak saliva pH of more than 8.5 during the first 120 seconds upon oral administration.

According to an embodiment of the invention the formulation provides a peak saliva pH of more than 9.0 during the first 120 seconds upon oral administration.

In an embodiment of the invention, the formulation provides a peak saliva pH of between 8.0 and 10.0 during the first 120 seconds upon oral administration.

In an embodiment of the invention, the formulation provides a peak saliva concentration of nicotine of more than 0.3 mg/mL and a peak saliva pH of more than 8 during the first 90 seconds upon oral administration.

In an embodiment of the invention, the formulation provides a peak saliva concentration of nicotine of more than 0.5 mg/mL and a peak saliva pH of more than 8 during the first 90 seconds upon oral administration.

In embodiments where the formulation provides a peak saliva concentration of nicotine of more than 0.3 mg/mL, such as more than 0.5 mg/mL, during the first 90 seconds upon oral administration, the amount of nicotine in the tablet should be adjusted to at least the amount necessary for obtaining this. Depending on the specific formulation, the amount of nicotine in the tablet may be higher than 0.5 mg in some embodiments, such as e.g. at least 1.0 mg or at least 2.0 mg.

According to an embodiment of the invention the formulation provides a peak saliva concentration of nicotine of more than 0.3 mg/mL and a peak saliva pH of more than 8 during the first 60 seconds upon oral administration.

According to an embodiment of the invention the formulation provides a peak saliva concentration of nicotine of more than 0.5 mg/mL and a peak saliva pH of more than 8 during the first 60 seconds upon oral administration.

In an embodiment of the invention, said oral nicotine formulation is provided as a solid formulation.

In an embodiment of the invention, the solid formulation comprises microcrystalline cellulose in an amount of 1-10% by weight of the solid formulation.

An advantage of the above embodiment is that a lower friability may be obtained without compromising the mouthfeel. Including too high amounts of microcrystalline cellulose may lead to a dusty mouthfeel.

According to an embodiment of the invention, the solid formulation comprises microcrystalline cellulose in an amount of 2-8% by weight of the solid formulation, such as 4-6% by weight of the solid formulation, such as about 5% by weight of the solid formulation.

In an embodiment of the invention, the oral nicotine formulation is provided in an orally disintegrating tablet.

In an embodiment of the invention, the oral nicotine formulation is provided in a sublingual orally disintegrating tablet.

In an embodiment of the invention, the tablet comprises sodium stearyl fumarate (SSF) as a lubricant.

An advantage of the above embodiment may be that it facilitates a shorter disintegration time of the tablet.

In an embodiment of the invention, said oral nicotine formulation is provided as a powder formulation.

In an embodiment of the invention, said oral nicotine formulation is provided in a pouch.

In an embodiment of the invention, the oral nicotine formulation is provided in a liquid mouth spray formulation.

In an embodiment of the invention, the formulation comprises a mucoadhesive.

Thus, the mucoadhesive facilitates the adherence to the oral mucosa. I.e. in the above embodiment, the adherence provided by the mouth spray formulation is facilitated or achieved by means said mucoadhesive.

In an embodiment of the invention, the mouth spray formulation comprises a mucoadhesive in the amount of between 1 and 50 mg/mL, such as in an amount of between 5 and 20 mg/mL.

In an embodiment of the invention, the mucoadhesive is selected from pectin, chitosan, alginate (e.g. sodium alginate), polyvinyl alcohol (PVA), polyacrylic acid (PAA), methyl cellulose (MC), sodium carboxy methylcellulose (SCMC), hydroxy propyl cellulose (HPC), preferably selected from the group consisting of pectin, PVA, PAA, xanthan gum, carbomer, carrageenan, and combinations thereof.

In an embodiment of the invention, the formulation is a sublingual liquid mouth spray formulation.

In an embodiment of the invention, the formulation is a sublingual formulation and/or the use comprises sublingual administration of the formulation.

This is even more advantageous, given the fact that very high concentrations of nicotine may be obtained sublingually with only minimum burning in the throat. A very high sublingually uptake thus both keeps the burning at a minimum and increases the nicotine uptake at the same time.

In an embodiment of the invention, the oral nicotine formulation is provided in a pouch.

In an embodiment of the invention, the oral nicotine formulation is provided in a pipetting formulation.

In an embodiment of the invention, the oral nicotine formulation is provided in a dropping formulation.

In an embodiment of the invention, the pouch, the pipetting formulation or dropping formulation is applied sublingually.

In an embodiment of the invention, the peak saliva concentration of nicotine is achieved over a period of at least 15 subsequent seconds within the first 120 seconds upon oral administering.

Thus, since the period has a length of at least 15 subsequent seconds, the period is a continuous period, i.e. not made of from two or more spaced apart periods. The period where the peak saliva concentration of nicotine is achieved may in some embodiment start immediately after oral administering, whereas in other embodiments the period starts later, but always such that the at least 15 subsequent seconds are within the first 120 seconds upon oral administering. Nevertheless, the peak saliva concentration of nicotine may extend beyond the first 120 seconds upon oral administering, provided that the peak saliva concentration of nicotine is achieved over a period of at least 15 subsequent seconds within the first 120 seconds upon oral administering.

According to an embodiment of the invention the peak saliva concentration of nicotine is achieved over a period of at least 30 subsequent seconds within the first 120 seconds upon oral administering.

In an embodiment of the invention, the peak saliva pH is achieved over a period of at least 15 subsequent seconds within the first 120 seconds upon oral administering.

Thus, since the period has a length of at least 15 subsequent seconds, the period is a continuous period, i.e. not made of from two or more spaced apart periods. The period where the peak saliva pH is achieved may in some embodiment start immediately after oral administering, whereas in other embodiments the period starts later, but always such that the at least 15 subsequent seconds are within the first 120 seconds upon oral administering. Nevertheless, the peak saliva pH may extend beyond the first 120 seconds upon oral administering, provided that the peak saliva pH is achieved over a period of at least 15 subsequent seconds within the first 120 seconds upon oral administering.

According to an embodiment of the invention the peak saliva pH is achieved over a period of at least 15 subsequent seconds within the first 120 seconds upon oral administering.

In an embodiment of the invention, the period where the peak saliva pH is achieved and the period where the peak saliva concentration of nicotine is achieved overlaps temporally by a period of at least 15 seconds.

In an embodiment of the invention, the nicotine formulation after administering to the oral cavity generates saliva, and at least a portion of said saliva is contained in the oral cavity in a period of at least 15 seconds prior to swallowing or spitting.

Thus, it should be understood that within the above embodiment, swallowing and spitting does not occur within said 15 seconds.

According to an embodiment of the invention, the at least 15 seconds prior to swallowing or spitting is the period where the peak saliva concentration of nicotine is achieved. Thus, in this embodiment the user does not swallow or spit before the end of the at least 15 subsequent seconds of a peak saliva concentration of nicotine of at least 0.3 mg/mL.

According to an embodiment of the invention, the at least 15 seconds prior to swallowing or spitting is the period where the peak saliva concentration of nicotine is achieved. Thus, in this embodiment the user does not swallow or spit before the end of the at least 15 subsequent seconds of a peak saliva concentration of nicotine of at least 0.5 mg/mL.

According to an embodiment of the invention, the at least 15 seconds prior to swallowing or spitting is the period where the peak saliva pH is achieved. Thus, in this embodiment the user does not swallow or spit before the end of the at least 15 subsequent seconds of a peak saliva pH of at least 7.5.

In an embodiment of the invention, at least a portion of said saliva is contained in the oral cavity in a period of at least 30 seconds prior to swallowing or spitting.

In an embodiment of the invention, nicotine is selected from the group consisting of a nicotine salt, the free base form of nicotine, a nicotine derivative, such as a nicotine cation exchanger, such as nicotine polacrilex resin, a nicotine inclusion complex or nicotine in any non-covalent binding; nicotine bound to zeolites; nicotine bound to cellulose, such as microcrystalline, or starch microspheres, and mixtures thereof.

In an embodiment of the invention, the nicotine is provided as a nicotine salt.

According to an embodiment of the invention, the nicotine salt is a water-soluble nicotine salt.

In the present context, the term "water-soluble salt" is understood as a salt having a solubility in water of at least 10 g of salt per 100 mL water at standard lab conditions, including temperature of 25 degrees Celsius, atmospheric pressure, and pH of 7.

Also, it should be understood that the when the nicotine is provided as nicotine salt, possibly in combination with nicotine free base, the nicotine salt may consist of only one nicotine salt, or may be a combination of two or more nicotine salts.

In an embodiment of the invention, the nicotine salt is selected from nicotine ascorbate, nicotine aspartate, nicotine benzoate, nicotine monotartrate, nicotine bitartrate, nicotine chloride (e.g., nicotine hydrochloride and nicotine dihydrochloride), nicotine citrate, nicotine fumarate, nicotine gensitate, nicotine lactate, nicotine mucate, nicotine laurate, nicotine levulinate, nicotine malate nicotine perchlorate, nicotine pyruvate, nicotine salicylate, nicotine sorbate, nicotine succinate, nicotine zinc chloride, nicotine sulfate, nicotine tosylate and hydrates thereof (e.g., nicotine zinc chloride monohydrate).

In an embodiment of the invention, the nicotine salt comprises nicotine bitartrate.

In the present context, nicotine bitartrate includes hydrates thereof.

According to an embodiment of the invention, the nicotine salt is nicotine bitartrate. In an embodiment of the invention, said nicotine is provided as a synthetic nicotine.

An advantage of the above embodiment may be that a more desirable taste profile may be obtained by avoiding undesirable taste notes that may be included in nicotine obtained from tobacco.

In an embodiment of the invention, said nicotine is provided as a complex between nicotine and an ion exchange resin.

In an embodiment of the invention, said complex between nicotine and the ion exchange resin is nicotine polacrilex resin (NPR).

In an embodiment of the invention, the nicotine is provided as free nicotine base.

In an embodiment of the invention, the nicotine is provided in association with a fatty acid.

In an embodiment of the invention, the nicotine is provided in ionic complex with at least one mucoadhesive water-soluble anionic polymer.

In an embodiment of the invention, the formulation comprises a mucoadhesive.

In an embodiment of the invention, the mucoadhesive is selected from pectin, chitosan, sodium alginate, polyvinyl alcohol (PVA), polyacrylic acid (PAA), methyl cellulose (MC), sodium carboxy methylcellulose (SCMC), hydroxy propyl cellulose (HPC), preferably selected from the group consisting of pectin, PVA, PAA, and combinations thereof.

In an embodiment of the invention, the formulation being designed to disintegrate within a period of less than 60 seconds upon oral administration.

In an embodiment of the invention, the formulation comprises at least one polyol and wherein the polyol comprises more than 40% by weight of the formulation.

In an embodiment of the invention, the formulation further comprises a disintegrant.

One advantage of the above embodiment may be that said disintegrant facilitates the disintegration and dissolution of the formulation, whereby a release of the nicotine and pH controlling agent is achieved. This is advantageous for solid formulations such as tablets and powdered formulations.

In an embodiment of the invention the formulation comprises disintegrant in an amount of 1-10% by weight of the formulation.

According to an embodiment of the invention, the formulation comprises disintegrant in an amount of 2-8% by weight of the formulation, such as 4-6% by weight of the formulation, such as about 5% by weight of the formulation.

Advantageously, the level of disintegrant is high enough to obtain a fast disintegration, but not too high as high amounts may increase production costs unnecessarily.

According to an embodiment of the invention, the disintegrant is selected from starch, pregelatinated starch, modified starch (including potato starch, maize starch, starch 1500, sodium starch glycolate and starch derivatives), cellulose, microcrystalline cellulose, alginates, ion-exchange resin, and superdisintegrants, such as crosslinked cellulose (such as sodium carboxy methyl cellulose), crosslinked polyvinyl pyrrolidone (PVP), crosslinked starch, crosslinked alginic acid, natural superdisintegrants, and calcium silicate, and combinations thereof.

In an embodiment of the invention the disintegrant comprises cross-linked polyvinylpyrrolidone.

In an embodiment of the invention the disintegrant is cross-linked polyvinylpyrrolidone.

An advantage of using cross-linked polyvinylpyrrolidone, also known as crospovidone, as disintegrant, may be that it decreases the dependence of the disintegration time on the compression force while allowing rather low disintegration times. This may be preferred especially for fast disintegrating tablets and powdered formulations. Also, for compressed tablets, by being more independent of compression force, a lower variation between tablets due to variations in compression force is facilitated.

In an embodiment of the invention at least 50% by weight of the cross-linked polyvinylpyrrolidone has a particle size below 50 micrometers.

This corresponds to commercial grades of crospovidone Kollidon CL-F and CL-SF.

In an embodiment of the invention at least 25% by weight of the cross-linked polyvinylpyrrolidone has a particle size below 15 micrometers.

This corresponds to commercial grade of crospovidone Kollidon CL-SF.

An advantage of the above embodiment of using cross-linked polyvinylpyrrolidone with a smaller particle size facilitates a shorter disintegration time, e.g. due to a larger relative surface of the disintegrant particles.

In an embodiment of the invention, the nicotine is not in ionic complex with a mucoadhesive water-soluble anionic polymer.

In an embodiment of the invention, the nicotine does not contain a nicotine complex.

In an embodiment of the invention, the oral nicotine formulation comprises a content of nicotine and a content of a pH regulating agent, wherein the formulation is adapted to provide a peak saliva concentration of nicotine of more than 0.5 mg/mL and a peak saliva pH of more than 8 during the first 120 seconds upon oral administration.

In an embodiment of the invention, the oral nicotine formulation comprises a content of nicotine and a content of a pH regulating agent, wherein the formulation is adapted to provide a peak saliva concentration of nicotine of more than 0.3 mg/mL and a peak saliva pH of more than 8 during the first 120 seconds upon oral administration.

In an embodiment of the invention, the formulation is provided as a tablet having a weight of 25 to 200 mg, such as 50 to 150 mg, such as 70-120 mg, such as about 75 mg or about 100 mg.

An advantage of the above embodiment may be that it provides a desirable low disintegration time, while allowing a sufficiently high nicotine amount to be included in the tablet.

In an embodiment of the invention, the formulation is provided as a powdered formulation is provided in an amount of 100 to 800 mg, such as 200 to 600 mg, such as about 400 mg.

In an embodiment of the invention, the formulation is provided as a liquid formulation providing a unit dosage of 20 to 300 microliter, such as 30 to 200 microliter, such as 40 to 170 microliter, such as 50 to 150 microliter, such as about 75 microliter.

In an embodiment of the invention the formulation comprises mannitol as a bulk sweetener.

In an embodiment of the invention, the formulation provides a peak saliva concentration of nicotine of more than more than 0.3 mg/mL, such as 0.5 mg/mL and a peak saliva pH of more than 7.5 during the first 120 seconds upon oral administration.

In an embodiment of the invention, the formulation provides a peak saliva concentration of nicotine of more than more than 0.3 mg/mL, such as 0.5 mg/mL and a peak saliva pH of more than 7.5 during the first 90 seconds upon oral administration.

In an embodiment of the invention, the formulation provides a peak saliva concentration of nicotine of more than more than 0.3 mg/mL, such as 0.5 mg/mL and a peak saliva pH of more than 7.5 during the first 60 seconds upon oral administration.

In an embodiment of the invention, the formulation provides a peak saliva concentration of nicotine of more than 0.3 mg/mL, such as more than 0.5 mg/mL during the first 90 seconds upon oral administration.

In an embodiment of the invention, the formulation provides a peak saliva concentration of nicotine of more than 0.3 mg/mL, such as more than 0.5 mg/mL during the first 60 seconds upon oral administration.

In an embodiment of the invention, the formulation provides a peak saliva pH of more than 7.5 during the first 90 seconds upon oral administration.

In an embodiment of the invention the formulation provides a peak saliva pH of more than 7.5 during the first 60 seconds upon oral administration, such as during the first 30 seconds upon oral administration.

In an embodiment of the invention the formulation provides a peak saliva concentration of nicotine of more than 0.3 mg/mL during the first 60 seconds upon oral administration, such as during the first 30 seconds upon oral administration.

In an embodiment of the invention the formulation provides a peak saliva concentration of nicotine of more than 0.5 mg/mL during the first 60 seconds upon oral administration, such as during the first 30 seconds upon oral administration.

In an embodiment of the invention the formulation provides a saliva concentration of nicotine of more than 0.3 mg/mL, such as more than 0.5 mg/mL, for a period of at least 20 seconds, such as at least 30 seconds, during the first 60 seconds upon oral administration.

The invention further relates to an oral nicotine formulation, the formulation comprising a content of nicotine and a content of a pH regulating agent, wherein the formulation is adapted to provide a peak saliva concentration of nicotine of more than 0.3 mg/mL and a peak saliva pH of more than 8 during the first 120 seconds upon oral administration.

Thus, according to the invention, the formulation is adapted to provide:
a peak saliva concentration of nicotine of more than 0.3 mg/mL and no more than 0.5 mg/mL and a peak saliva pH of more than 8 during the first 120 seconds upon oral administration, or
a peak saliva concentration of nicotine of more than 0.5 mg/mL and a peak saliva pH of more than 8 during the first 120 seconds upon oral administration.

In an embodiment of the invention, the formulation is adapted to provide a peak saliva concentration of nicotine of more than 0.5 mg/mL and a peak saliva pH of more than 8 during the first 120 seconds upon oral administration.

In an embodiment of the invention, the oral nicotine formulation of the invention is further usable as the oral nicotine formulation for use in the alleviation of nicotine craving according to the invention and any of its embodiments.

It should be understood that the oral nicotine formulation of the above embodiment is not limited to any particular use, such as an oral nicotine formulation for use in the alleviation of nicotine craving, but is directed to the oral nicotine formulation as such.

According to an embodiment of the invention, the oral nicotine formulation for use in the alleviation of nicotine craving comprises a content of nicotine and a content of a pH regulating agent, wherein the formulation provides a peak saliva concentration of nicotine of more than 0.3 mg/mL, such as more than 0.5 mg/mL, and a peak saliva pH of more than 7.5 during the first 120 seconds upon oral administration, and wherein the oral nicotine formulation comprises nicotine in an amount of at least 0.5 mg.

According to an embodiment of the invention, the oral nicotine formulation for use in the alleviation of nicotine craving comprises a content of nicotine and a content of a pH regulating agent, wherein the formulation provides a peak saliva concentration of nicotine of more than 0.3 mg/mL, such as more than 0.5 mg/mL, and a peak saliva pH of more than 7.5 during the first 120 seconds upon oral administration, wherein the oral nicotine formulation comprises nicotine in an amount of at least 0.5 mg, and wherein said oral nicotine formulation is provided in an orally disintegrating tablet.

According to an embodiment of the invention, the oral nicotine formulation for use in the alleviation of nicotine craving comprises a content of nicotine and a content of a pH regulating agent, wherein the formulation provides a peak saliva concentration of nicotine of more than 0.3 mg/mL, such as more than 0.5 mg/mL, and a peak saliva pH of more than 7.5 during the first 120 seconds upon oral administration, wherein the oral nicotine formulation comprises nicotine in an amount of at least 0.5 mg, and wherein said oral nicotine formulation is provided in a sublingual orally disintegrating tablet.

According to an embodiment of the invention, the oral nicotine formulation for use in the alleviation of nicotine craving comprises a content of nicotine and a content of a pH regulating agent, wherein the formulation provides a peak saliva concentration of nicotine of more than 0.3 mg/mL, such as more than 0.5 mg/mL, and a peak saliva pH of more than 7.5 during the first 120 seconds upon oral administration, and wherein said oral nicotine formulation is provided in a sublingual orally disintegrating tablet.

According to an embodiment of the invention, the oral nicotine formulation for use in the alleviation of nicotine craving comprises a content of nicotine and a content of a pH regulating agent, wherein the formulation provides a peak saliva concentration of nicotine of more than 0.3 mg/mL, such as more than 0.5 mg/mL, and a peak saliva pH of more than 7.5 during the first 120 seconds upon oral administration, wherein the oral nicotine formulation comprises nicotine in an amount of at least 0.5 mg, and wherein said oral nicotine formulation is provided in a liquid mouth spray formulation.

According to an embodiment of the invention, the oral nicotine formulation for use in the alleviation of nicotine craving comprises a content of nicotine and a content of a pH regulating agent, wherein the formulation provides a peak saliva concentration of nicotine of more than 0.3 mg/mL, such as more than 0.5 mg/mL, and a peak saliva pH of more than 7.5 during the first 120 seconds upon oral administration, wherein the oral nicotine formulation comprises nicotine in an amount of at least 0.5 mg, and wherein said nicotine is provided as a nicotine salt.

According to an embodiment of the invention, the oral nicotine formulation for use in the alleviation of nicotine craving comprises a content of nicotine and a content of a pH regulating agent, wherein the formulation provides a peak saliva concentration of nicotine of more than 0.3 mg/mL, such as more than 0.5 mg/mL, and a peak saliva pH of more than 7.5 during the first 120 seconds upon oral administration, wherein the oral nicotine formulation comprises nicotine in an amount of at least 0.5 mg, wherein said oral nicotine formulation is provided in an orally disintegrating tablet, and wherein said nicotine is provided as a nicotine salt.

According to an embodiment of the invention, the oral nicotine formulation for use in the alleviation of nicotine craving comprises a content of nicotine and a content of a pH regulating agent, wherein the formulation provides a peak saliva concentration of nicotine of more than 0.3 mg/mL, such as more than 0.5 mg/mL, and a peak saliva pH of more than 7.5 during the first 120 seconds upon oral administration, wherein the oral nicotine formulation comprises nicotine in an amount of at least 0.5 mg, wherein said oral nicotine formulation is provided in a sublingual orally disintegrating tablet, and wherein said nicotine is provided as a nicotine salt.

According to an embodiment of the invention, the oral nicotine formulation for use in the alleviation of nicotine craving comprises a content of nicotine and a content of a pH regulating agent, wherein the formulation provides a peak saliva concentration of nicotine of more than 0.3 mg/mL, such as more than 0.5 mg/mL, and a peak saliva pH of more than 7.5 during the first 120 seconds upon oral administration, wherein said oral nicotine formulation is provided in a sublingual orally disintegrating tablet, and wherein said nicotine is provided as a nicotine salt.

According to an embodiment of the invention, the oral nicotine formulation for use in the alleviation of nicotine craving comprises a content of nicotine and a content of a pH regulating agent, wherein the formulation provides a peak saliva concentration of nicotine of more than 0.3 mg/mL, such as more than 0.5 mg/mL, and a peak saliva pH of more than 7.5 during the first 120 seconds upon oral administration, wherein the oral nicotine formulation comprises nicotine in an amount of at least 0.5 mg, wherein said oral nicotine formulation is provided in a liquid mouth spray formulation, and wherein said nicotine is provided as a nicotine salt.

Moreover, the invention relates to a method of alleviation of nicotine craving by administering an effective amount of said oral nicotine formulation according to the invention or any of its embodiments.

DETAILED DESCRIPTION

As used herein, the term "orally disintegrating tablet" refers to a tablet for oral administering which disintegrates in the oral cavity relatively fast from the administering, such as within about three minutes from oral administering. Orally disintegrating tablets may be intended for use as a sublingual tablet for positioning under the tongue, as a buccal tablet, as a tablet for melting on the tongue, or for other types of oral administering.

Orally disintegrating tablets may also be referred to "orally dissolving tablets", and these two terms are used interchangeably herein. Commonly, these terms are also referred to by their abbreviation, ODT. Similarly, the terms "fast dissolving tablet" and "fast disintegrating tablet", as well as the abbreviation FDT, refers herein to an orally disintegrating tablet.

As used herein the term "liquid mouth spray formulation" refers to a mouth spray for application of drug orally, e.g. either sublingually or buccal. The mouth spray formulation is provided as a liquid, but may comprise gelling agents for forming a gel during/after administering to the oral cavity. Liquid mouth spray formulation may also be referred to as fast acting mouth spray.

As used herein, the term "disintegrate" refers to a reduction of a said object to components, fragments or particles. Disintegration time is measured in vitro. The in vitro measurements are carried out in accordance to European Pharmacopeia 9.0, section 2.9.1, Disintegration of tablets and capsules.

As used herein, the term "dissolve" refer to the process where a solid substance enters a solvent (oral saliva) to yield a solution, or the process of a liquid formulation being mixed with and thus dissolved in the saliva. Unless otherwise stated, dissolving implies a full dissolving of the compound in question.

As used herein, the term "mouth spray" refers to a small pump-type or squeeze-type container having a spray nozzle and contains a liquid (mouth spray) to be sprayed into the mouth.

As used herein, the terms "disintegrant" refers to an ingredient facilitating disintegration of an orally disintegrating tablet, when the orally disintegrating tablet comes into contact with saliva. Disintegrants usable within the scope of the invention may include starch, pregelatinated starch, modified starch (including potato starch, maize starch, starch 1500, sodium starch glycolate and starch derivatives), cellulose, microcrystalline cellulose, alginates, ion-exchange resin, and superdisintegrants, such as crosslinked cellulose (such as sodium carboxy methyl cellulose), crosslinked polyvinyl pyrrolidone (PVP), crosslinked starch, crosslinked alginic acid, natural superdisintegrants, and calcium silicate. Disintegrants may often be considered as measure promoting the break-up of the dosage form into smaller fragments upon administration to allow the onset of drug dissolution and eventual absorption.

As used herein, the term "nicotine" refers to nicotine in any form, including free base nicotine, nicotine salts, nicotine bound to ion exchange resins, such as nicotine polacrilex, nicotine bound to zeolites; nicotine bound to cellulose, such as microcrystalline cellulose, such as of microbial origin, or starch microspheres, nicotine bound to $CaCO_3$, and mixtures thereof. Thus, when referring to nicotine amounts, the amounts refers to the amount of pure nicotine. Thus, when measuring the concentration of nicotine added as nicotine salt, it is the mass of the equivalent amount of pure nicotine, not the mass of the salt, that is relevant. Nicotine also covers nicotine not obtained from tobacco, often referred to as synthetic nicotine.

As used herein, the term "nicotine salt" refers to nicotine in ionized form bonded electrostatically to a counterion.

As used herein, the term "NBT" refers to nicotine bitartrate and hydrates thereof.

As used herein, the term "%" and "percent" refers to percent by weight, unless otherwise is stated.

As used herein, the term "release of nicotine" refers to the nicotine being made bioavailable, i.e. available for absorption over the mucous membrane in the oral cavity. While some forms of nicotine require dissolution for being bioavailable, other forms may be readily absorbed into the body without dissolution. For example, for solid compositions, in order for the nicotine to be bioavailable, the matrix of the solid formulation should be disintegrated. Some forms of nicotine require the nicotine to further be released from e.g. a carrier, e.g. nicotine from a nicotine-ion exchange resin such as nicotine polacrilex. Other nicotine forms, such nicotine salts, hereunder nicotine bitartrate, may readily dissolve upon disintegration of the matrix of the solid formulation. Still, some nicotine forms may not require dissolving. This applies for e.g. nicotine free base, which is released upon disintegration of the solid formulation matrix.

As used herein, the term "peak saliva concentration of nicotine" refers to the peak value of the concentration of nicotine in saliva of the oral cavity, where the saliva includes delivery vehicle of the nicotine dissolved therein, e.g. liquid mouth spray formulation dissolved in the saliva. Also, it should be understood that the peak saliva concentration is considered to be achieved whenever the criterion is fulfilled, i.e. when the concentration of nicotine exceeds the stated nicotine concentration. E.g. if a peak saliva concentration of nicotine is at least 0.5 mg/mL, this peak saliva concentration is achieved whenever the concentration of nicotine exceeds 0.5 mg/mL. Measurements of peak saliva nicotine concentration are done in vivo and the measurements are performed as follows:

One dosage of the formulation is administered sublingually to at least six individuals. At specified time intervals, the saliva is collected. The experiment is repeated. Thus, each nicotine concentration value is the arithmetic mean of 12 measurements, i.e. performed on saliva-samples from six individuals times 2. The nicotine concentration of saliva is analyzed on HPLC after extraction into relevant buffer.

For liquid formulations, the peak saliva concentration of nicotine is measured after 1 unit dose of the liquid formulation is dispensed to the oral cavity. For tableted formulations, the peak saliva concentration of nicotine is measured after 1 tablet is dispensed to the oral cavity. For other formulations, such as powder formulations, the peak saliva concentration of nicotine is measured after 1 dose of the powder formulation (typically 100-800 mg) is dispensed to the oral cavity.

As used herein, the term "peak saliva pH" refers to the peak value of the pH in saliva of the oral cavity, where the saliva includes any delivery vehicle of the pH regulating agent, such as e.g. liquid mouth spray formulations etc. Also, it should be understood that the peak saliva pH is considered to be achieved whenever the criterion is fulfilled. E.g. if a peak saliva pH is at least 7.5, this peak saliva pH is achieved whenever the pH exceeds 7.5. Peak saliva pH is measured in vivo and is measured as follows: At least 6 individuals chewed on a gum base free of buffer for 1 minute, after which the initial pH in a sample from the saliva from each of the individuals is measured with a suitable pH-electrode system, e.g. a stainless steel electrode PHW77-SS. Only individuals having, after chewing on a gum base free of buffer for one minute, an initial pH in the saliva inside the range from 6.7 and 7.3 are selected. These individuals thereby qualify as average individuals.

One dosage of the formulation is administered sublingually to at least six individuals. Hereafter, the saliva pH from each of the six individuals is measured at specified time intervals. Thus, each pH-value is the arithmetic mean of six measurements performed on saliva-samples from six individuals.

For liquid formulations, the peak saliva concentration of nicotine is measured after 1 unit dose of the liquid formulation is dispensed to the oral cavity. For tableted formulations, the peak saliva concentration of nicotine is measured after 1 tablet is dispensed to the oral cavity. For other formulations, such as powder formulations, the peak saliva concentration of nicotine is measured after 1 dose of the powder formulation (typically 100-800 mg) is dispensed to the oral cavity.

As used herein, the term "pH regulating agent" refers to agents, which active adjust and regulates the pH value of the solution to which they have been added or are to be added. Thus, pH regulating agents may be acids and bases, including acidic buffering agents and alkaline buffering agents. On the other hand, pH regulating agents does not including substances and compositions that can only affect the pH by dilution. Furthermore, pH regulating agents does not include e.g. flavoring, fillers, etc.

As used herein, the term "buffering agent" is used interchangeably with "buffer" and refers to agents for obtaining a buffer solution. Buffering agents include acidic buffering agents, i.e. for obtaining a buffer solution with an acidic pH, and alkaline buffering agents, i.e. for obtaining a buffer solution with an alkaline pH.

As used herein, the term "fast onset nicotine craving relief" refers to relief of nicotine craving, for which the onset is relatively fast, i.e. only a relatively short period of time after oral administering. In embodiments of the invention, the fast onset refers to a period after oral administration until craving relief is experienced being no more than 180 seconds, such as no more than 120 seconds, such as no more than 60 seconds.

EXAMPLES

The following non-limiting examples illustrate different variations of the present invention.

Example 1

Preparation of Fast Acting Mouth Spray

In the present example six fast acting mouth spray are prepared with formulations as outlined in table 1. Four of the fast acting mouth spray are prepared with pure nicotine base and two is placebo. The three first batches contain no buffer whereas the last three batches contains buffer. Some of the six batches are adjusted with pH regulating agents for obtaining pH 9.0 of the final mixture. See further explanation in table 2.

TABLE 1

High level description of Fast acting mouth spray compositions.

| | Description of trial |
|---|---|
| FAM(a) | No buffer system - Placebo trial |
| FAM(b) | No buffer system - pH adjusted to 9.0 |
| FAM(c) | No buffer system - not adjusted |
| FAM(d) | Buffer system - Placebo trial |
| FAM(e) | Buffer system - pH adjusted to 9.0 |
| FAM(f) | Buffer system - not adjusted |

TABLE 2

Fast acting mouth spray compositions. Amounts are given in percent by weight of each composition.

| | FAM (a) | FAM (b) | FAM (c) | FAM (d) | FAM (e) | FAM (f) |
|---|---|---|---|---|---|---|
| Nicotine base | N/A | 1.43 | 1.43 | N/A | 1.43 | 1.43 |
| Dem. water | 60.9 | 59.47 | 59.47 | 58.5 | 57.07 | 57.07 |
| Poloxamer 407 | 3.0 | 3.0 | 3.0 | 3.0 | 3.0 | 3.0 |
| Propylene glycol | 12.5 | 12.5 | 12.5 | 12.5 | 12.5 | 12.5 |
| Glycerine | 12.5 | 12.5 | 12.5 | 12.5 | 12.5 | 12.5 |
| Peppermint | 0.30 | 0.30 | 0.30 | 0.30 | 0.30 | 0.30 |
| Menthol | 0.50 | 0.50 | 0.50 | 0.50 | 0.50 | 0.50 |
| Acesulfame K | 0.20 | 0.20 | 0.20 | 0.20 | 0.20 | 0.20 |
| Sucralose | 0.1 | 0.1 | 0.1 | 0.1 | 0.1 | 0.1 |
| Sodium carbonate | — | — | — | 1.2 | 1.2 | 1.2 |
| Trometamol | — | — | — | 1.2 | 1.2 | 1.2 |
| Ethanol | 10.0 | 10.0 | 10.0 | 10.0 | 10.0 | 10.0 |
| Total | 100.0 | 100.0 | 100.0 | 100.0 | 100.0 | 100.0 |

FAM = Fast acting mouth spray.

The fast acting mouth spray are manufactured on a lab scale using a bench scale magnetic stirrer. The assay, in vitro pH and viscosity are measured after manufacture to ensure they match the acceptance criteria.

Raw materials are weighed from bags or containers into separate weighing containers except for demineralized water. The batch size is 210 grams.

Preparing the Mixture:

Demineralized water of room temperature is added to a blue cap bottle (size 2×expected batch volume). Add a stir bar (magnet) and place the glass bottle on a magnetic stirrer. No heating is needed. Add surfactant (for example Poloxamer 407) slowly to the water while stirring. Stir until it is dissolved. Add all other excipients for and stir until fully dissolved.

Nicotine base is added using a 3.0 ml glass pipette, and the liquid is stirred for at least 5 minutes with stirring showing visible vortex. The pH of the solution is measured. The pH of the final mixture is checked and where applicable adjusted to pH 9.0 with 2 M HCl or 2 M NaOH. The liquid is stirred during addition and the mixture is stirred for 5 minutes. The pH of the final mixture is measured and results are shown in table 3.

TABLE 3 pH in final mixture of FAM(a-f)

| | Mixture pH | | |
|---|---|---|---|
| | Before addition of nicotine base | After addition of nicotine base | Adjustment of pH |
| FAM(a) | 6.73 | — | — |
| FAM(b) | — | 9.85 | 9.01 |
| FAM(c) | — | 9.95 | — |
| FAM(d) | 9.32 | — | — |
| FAM(e) | — | 9.41 | 9.01 |
| FAM(f) | — | 9.42 | — |

The liquid is filled into HDPE or PET bottles. The filling volume is checked by weight. The bottle is closed with a pump spray head with an output volume of 70 microliters in this case corresponding to a final dose of 1 mg nicotine due to the nicotine concentration of the liquid being 14.3 mg/ml. The output volume could be adjusted from 50 to 150 microliters with or without changing the nicotine concentration of the liquid.

The fast acting mouth spray according to the invention may comprise coloring agents. According to an embodiment of the invention, the fast acting mouth sprays may comprise color agents and whiteners such as FD&C-type dyes and lakes, fruit and vegetable extracts, and combinations thereof.

Example 2

Preparation of Fast Acting Mouth Spray with Different Concentrations

In the present example six fast acting mouth sprays are prepared with formulations as outlined in table 4A. The fast acting mouth spray is prepared with nicotine pure base. The methodology for manufacture is similar to the description in example 1.

TABLE 4A

Fast acting mouth spray compositions. Amounts are given in percent by weight of each composition.

| | FAM (g) | FAM (h) | FAM (i) | FAM (j) | FAM (k) | FAM (l) |
|---|---|---|---|---|---|---|
| Nicotine base | 0.72 | 1.43 | 2.86 | 0.72 | 1.43 | 2.86 |
| Dem. water | 60.18 | 59.47 | 58.04 | 58.38 | 57.67 | 56.24 |
| Poloxamer 407 | 3.0 | 3.0 | 3.0 | 3.0 | 3.0 | 3.0 |
| Propylene glycol | 12.5 | 12.5 | 12.5 | 12.5 | 12.5 | 12.5 |
| Glycerine | 12.5 | 12.5 | 12.5 | 12.5 | 12.5 | 12.5 |
| Peppermint | 0.3 | 0.3 | 0.3 | 0.3 | 0.3 | 0.3 |
| Menthol | 0.1 | 0.1 | 0.1 | 0.1 | 0.1 | 0.1 |
| Acesulfame K | 0.2 | 0.2 | 0.2 | 0.2 | 0.2 | 0.2 |
| Sucralose | 0.1 | 0.1 | 0.1 | 0.1 | 0.1 | 0.1 |
| Trometamol | — | — | — | 1.35 | 1.35 | 1.35 |
| Sodium bicarbonate | — | — | — | 0.45 | 0.45 | 0.45 |
| Ethanol 96% | 10.4 | 10.4 | 10.4 | 10.4 | 10.4 | 10.4 |
| Total | 100.0 | 100.0 | 100.0 | 100.0 | 100.0 | 100.0 |

FAM = Fast acting mouth spray.

Further, three additional fast acting mouth sprays comprising mucoadhesive are prepared with formulations as outlined in table 4A. The fast acting mouth spray is prepared with pure, free nicotine base. The methodology for manufacture is similar to the description in example 1.

TABLE 4B

Fast acting mouth spray compositions.

| | FAM (m) | FAM (n) | FAM (o) |
|---|---|---|---|
| Nicotine base | 0.72 | 1.43 | 2.86 |
| Dem. water | 59.18 | 58.47 | 57.04 |
| Poloxamer 407 | 3.0 | 3.0 | 3.0 |
| Propylene glycol | 12.5 | 12.5 | 12.5 |
| Glycerine | 12.5 | 12.5 | 12.5 |
| Peppermint | 0.3 | 0.3 | 0.3 |
| Menthol | 0.1 | 0.1 | 0.1 |
| Acesulfame K | 0.2 | 0.2 | 0.2 |
| Sucralose | 0.1 | 0.1 | 0.1 |
| Sodium alginate | 1.0 | 1.0 | 1.0 |
| Ethanol 96% | 10.4 | 10.4 | 10.4 |
| Total | 100.0 | 100.0 | 100.0 |

Amounts are given in percent by weight of each composition.
FAM = Fast acting mouth spray.

As can be seen in table 2, demineralized water, propylene glycol, glycerine, and ethanol 96% are used as pharmaceutically acceptable solvents. As can be seen in table 4A-4B, demineralized water, propylene glycol, and glycerine are used as pharmaceutically acceptable solvents. Examples of usable pharmaceutically acceptable solvents include water; terpenes, such as menthol; alcohols, such as ethanol, propylene glycol, polyethylene glycol, such as PEG 400, glycerol and other similar alcohols; and mixtures or combinations thereof.

In an embodiment of the invention, the pharmaceutically acceptable solvents comprise propylene glycol.

In an embodiment of the invention, the pharmaceutically acceptable solvents comprise PEG 400.

In an embodiment of the invention, the pharmaceutically acceptable solvents comprise glycerol.

In an embodiment of the invention, the pharmaceutically acceptable solvents comprise ethanol.

In an embodiment of the invention, the pharmaceutically acceptable solvents comprise water.

In an embodiment of the invention, said liquid formulation comprises glycerol in an amount of 0-40% by weight, such as 0.01-40% by weight, such as 0.1-40% by weight.

In an embodiment of the invention, said liquid formulation comprises propylene glycol in an amount of 0-40 by weight, such as 0.01-40% by weight, such as 0.1-40% by weight.

In an embodiment of the invention, said liquid formulation comprises 0.1-70% by weight of water, such as 0.1-60% by weight of water, such as 0-10% by weight of water, or such as 30-50% by weight of water.

As can be seen in table 4A-4B, peppermint and menthol are used as flavors. Usable flavors include almond, almond amaretto, apple, Bavarian cream, black cherry, black sesame seed, blueberry, brown sugar, bubblegum, butterscotch, cappuccino, caramel, caramel cappuccino, cheesecake (graham crust), cinnamon redhots, cotton candy, circus cotton candy, clove, coconut, coffee, clear coffee, double chocolate, energy cow, graham cracker, grape juice, green apple, Hawaiian punch, honey, Jamaican rum, Kentucky bourbon, kiwi, koolada, lemon, lemon lime, tobacco, maple syrup, maraschino cherry, marshmallow, menthol, milk chocolate, mocha, Mountain Dew, peanut butter, pecan, peppermint, raspberry, banana, ripe banana, root beer, RY 4, spearmint, strawberry, sweet cream, sweet tarts, sweetener, toasted almond, tobacco, tobacco blend, vanilla bean ice cream, vanilla cupcake, vanilla swirl, vanillin, waffle, Belgian waffle, watermelon, whipped cream, white chocolate, wintergreen, amaretto, banana cream, black walnut, blackberry, butter, butter rum, cherry, chocolate hazelnut, cinnamon roll, cola, creme de menthe, eggnog, English toffee, guava, lemonade, licorice, maple, mint chocolate chip, orange cream, peach, pina colada, pineapple, plum, pomegranate, pralines and cream, red licorice, salt water taffy, strawberry banana, strawberry kiwi, tropical punch, tutti frutti, vanilla, or any combination thereof.

According to an advantageous embodiment of the invention, said liquid formulation comprises 0.01-5% by weight of flavoring, such as 0.01-2.5% by weight of flavoring, 0.01-0.5% by weight of flavoring.

According to an embodiment of the invention, flavor may be used as taste masking for the nicotine.

In embodiments of the invention, the formulation comprises pH regulating agent in an amount of from 0.5% to 5.0% by weight of the formulation.

In an embodiment of the invention, the pH regulating agent comprises buffering agent.

As can be seen in table 2, sodium carbonate and trometamol are used as buffering agents. In table 4, trometamol and sodium bicarbonate are used as buffering agents. Usable buffering agents include carbonates, including monocarbonate, bicarbonate and sesquicarbonate, glycerinate, phosphate, glycerophosphate, acetate, glyconate or citrate of an alkali metal, ammonium, tris buffer, amino acids and mixtures thereof.

Buffering agent may be added to the mouth spray formulation together with water-soluble mouth spray formulation ingredients. When suitable amounts of buffering agent is added to the mouth spray formulation as part of the water-soluble mouth spray formulation ingredients, a pH-profile according to embodiments of the present invention can be obtained.

Buffering agent may be used in the mouth spray formulation to contribute to the desired pH-values in the saliva of a user.

A preferred buffering agent according to advantageous embodiments of the present invention is the sodium carbonate-sodium bicarbonate buffer system.

As can be seen in table 2, acesulfame K and sucralose are used as high intensity sweeteners. Usable high intensity sweeteners include, but are not limited to sucralose, aspartame, salts of acesulfame, such as acesulfame potassium, alitame, saccharin and its salts, cyclamic acid and its salts, glycyrrhizin, dihydrochalcones, thaumatin, monellin, stevioside and the like, alone or in combination.

In embodiments of the invention, the liquid formulation comprise one or more fast acting mouth spray ingredients selected from the group consisting solvents, flavors, surfactants, emulsifiers, antioxidants, enhancers, carriers, absorption enhancers, buffers, high intensity sweeteners, mucoadhesives, colors, or any combination thereof.

As can be seen in table 2, poloxamer 407 is used as a surfactant. Other surfactants may also be used within the scope of the invention.

In embodiments of the invention, usable emulsifiers include, but are not limited to, the emulsifiers are selected from the group consisting of glyceryl monostearate, propylene glycol monostearate, mono- and diglycerides of edible fatty acids, lactic acid esters and acetic acid esters of mono- and diglycerides of edible fatty acids, acetylated mono and diglycerides, sugar esters of edible fatty acids, Na-, K-, Mg- and Ca-stearates, poloxamer 407, lecithin, hydroxylated lecithin and combinations thereof.

In an embodiment of the invention, the mucoadhesive is selected from pectin, chitosan, alginate (e.g. sodium alginate), polyvinyl alcohol (PVA), polyacrylic acid (PAA), methyl cellulose (MC), sodium carboxy methylcellulose (SCMC), hydroxy propyl cellulose (HPC), preferably selected from the group consisting of pectin, PVA, PAA, xanthan gum, carbomer, carrageenan, and combinations thereof.

Example 3

In Vivo pH Profile

Table 5A shows the pH profiles over time for a number of fast acting mouth spray as well as for a commercially available mouth spray. The nicotine mouth spray reveals also fast craving relief

TABLE 5A

| pH In vivo measurements. | | | | |
| --- | --- | --- | --- | --- |
| Time (min) | Pretest | 0 | 1 | 3 |
| Commercial mouth spray | 7.1 | 8.3 | 7.5 | 7.2 |
| FAM(a) | 6.9 | 7.1 | 7.1 | 7.0 |
| FAM(b) | 7.0 | 7.8 | 7.3 | 7.1 |
| FAM(c) | 7.0 | 7.7 | 7.3 | 7.2 |
| FAM(d) | 7.0 | 8.1 | 7.3 | 7.1 |
| FAM(e) | 7.0 | 8.2 | 7.3 | 7.1 |
| FAM(f) | 7.1 | 8.1 | 7.4 | 7.2 |

The measurements of the average in vivo pH values given in Table 5A were performed as follows:

At least 6 individuals chewed on a gum base free of buffer for 1 minute, after which the initial pH in a sample from the saliva from each of the individuals was measured with a suitable pH-electrode system, e.g. a stainless steel electrode PHW77-SS. None of the individuals had, after chewing on a gum base free of buffer for one minute, an initial pH in the saliva outside the range from 6.7 and 7.3. The individuals thereby qualified as average individuals.

Then the six individuals applied one dose of the fast acting mouth spray sublingually. Hereafter the saliva pH from each of the six individuals was measured at specified time intervals. Thus, each pH-value in Table 5A is the arithmetic mean of six measurements performed on saliva-samples from six individuals. The sample volume of the individual saliva-samples may vary because the volume of saliva obtained may be different from each individual. This difference in sample volume does not affect the pH-measurements significantly. Also, it has been established by appropriate tests that a variation in time between collections of samples does not significantly alter the result. This means that the measured pH-value after three minutes is not significantly affected by whether another saliva-sample is taken from the six individuals e.g. after two minutes or not. Furthermore, it has been established by appropriate tests that the time from taking a sample to the time of measuring is not critical to the measured value. However, in the present measurements, the pH-values were measured in the samples within at most 15 minutes of sample collection.

It should be noted that the in vivo pH-profile is different from an in vitro pH-profile due to the fact that acidic sodium bicarbonate is normally continuously produced in saliva, hence neutralizing the alkaline contribution from buffer. Thus, the pH obtained in vivo will be lower than in vitro measured in a beaker with stirring.

Example 4

Nicotine Concentration in Saliva

The measurements of the average nicotine concentration in saliva were performed as follows:

At least six individuals applied one dose of the fast acting mouth spray sublingually given in example 2. After 30 seconds, the saliva was collected. The experiment was repeated. Thus, each nicotine concentration value is the arithmetic mean of 12 measurements, i.e. performed on saliva-samples from six individuals times 2. The nicotine concentration of saliva was analyzed on HPLC after extraction into relevant buffer. Furthermore, compared to a commercially available mouth spray.

It is seen that the release of nicotine may vary a lot between the disclosed fast acting mouth spray. Hereby a release profile as desired may be used together with a high pH (as seen in example 3), whereby the nicotine may be more efficiently used.

Obtained in vivo saliva concentrations of nicotine are outlined in table 5B.

TABLE 5B

Nicotine concentration in saliva after 1 spray dose for mouthsprays FAM(h), FAM(i), FAM(k), FAM(l) and Nicorette Quickmist

| | FAM(h) | FAM(i) | FAM(k) | FAM(l) | Nicorette Quickmist |
|---|---|---|---|---|---|
| Nicotine per spray dose | 1 mg | 2 mg | 1 mg | 2 mg | 1 mg |
| Nicotine concentration [mg/mL] | 0.51 | 1.03 | 0.49 | 0.95 | 0.40 |

As can be seen from table 5B, a nicotine concentration of about 1 mg/mL is obtained by FAM(i) without using buffer. FAM(l), including buffer, results in a similar nicotine concentration. The same trend is observed when comparing FAM(h) without buffer and FAM(k) with buffer. Thus, the liquid mouthspray formulations of the invention are desirable for obtaining a peak saliva nicotine concentration of more than 0.5 mg/mL. The obtained in vivo saliva nicotine concentrations were slightly higher than for the commercial mouthspray having corresponding nicotine dose per spray.

Example 5A

Evaluation of Fast Acting Mouth Spray—Burning

In general experiments have disclosed that nicotine fast acting mouth spray according to the invention result in high absorption efficiency of nicotine into the blood stream for a nicotine fast acting mouth spray. With such fast integration, high pH-value combined with high nicotine concentration, a minor part of the nicotine is swallowed by the user instead of entering the blood system resulting in fast craving relief.

When pH in the mouth is high, the nicotine is used in a very efficient way. However, too high pH in the saliva of the fast acting mouth spray users may not be desirable, since the highly alkaline pH-value results in problems with irritation and burning of the sublingual tissue.

Consequently, the fast acting mouth spray of the invention are indeed suitable in that they provide an efficient utilization of nicotine and at the same time are pleasant to the user, i.e. with clearly diminished unwanted side effects, hereunder particularly burning in the throat.

Burning in the throat was evaluated for FAM(h) and Nicorette Quickmist. A predetermined dose corresponding to 1 mg nicotine is administered to the oral cavity as indicated in table 5C. Evaluation of burning sensation is performed as described in the following.

Burning in the throat was evaluated by a test panel of 5 trained individuals. Each individual evaluates the burning from 1 to 15, where 15 is the most intense burning.

The evaluations are noted for the time periods indicated. Average values are calculated and are indicated in table 5C.

TABLE 5C

Sensory evaluation of throat burning.

| | Time [seconds] | | | | | |
|---|---|---|---|---|---|---|
| | 25 | 55 | 85 | 120 | 145 | 175 |
| | | | Burning score (1-15) | | | |
| FAM(h) | 0.92 | 3.25 | 3.85 | 3.75 | 3.74 | 3.57 |
| Nicorette Quickmist | 1.53 | 6.55 | 6.67 | 6.58 | 6.21 | 5.92 |

As can be seen from table 5C, the mouthspray FAM(h) of the invention gives significantly lower burning than the comparison mouthspray. Thus, the liquid mouthspray formulations of the invention supports obtaining a low throat burning sensation.

Example 5B

Nicotine Absorption

Nicotine absorption was tested in vivo for FAM(h), FAM(i), FAM(k), FAM(l) and commercially available Nicorette Quickmist. A predefined spray dose of 70 microliters corresponding to 1 or 2 mg nicotine was administered to the oral cavity, as outlined in table 8.

No swallowing was allowed within the first 30 seconds. The saliva is collected after 30 seconds in 50 mL centrifugal tubes. These are analysed to determine the content of nicotine. The absorption is estimated as the difference between initial dose and the content of nicotine in saliva.

The results are shown in table 5D.

TABLE 5D

Nicotine absorption.

| Batch no. | Nicotine concentration in spray [mg/g] | Nicotine per spray Dose [mg] | Buffer | % wt. absorbed |
|---|---|---|---|---|
| FAM(h) | 14.3 | 1.0 | No buffer | 51 |
| FAM(i) | 28.6 | 2.0 | No buffer | 48 |
| FAM(k) | 14.3 | 1.0 | Buffer | 53 |
| FAM(l) | 28.6 | 2.0 | Buffer | 53 |
| Nicorette QuickMist | 14.3 | 1.0 | Buffer: Trometamol, Sodium hydrogen carbonate | 60 |

It is noted that nicotine absorption was above 40% by weight, and for FAM(h) even above 50% by weight. Also, when comparing the mouthsprays FAM(h)-FAM(i) with corresponding mouthsprays comprising buffer, FAM(k)-FAM(l), the nicotine absorption of FAM(h)-FAM(i) is only slightly below that of FAM(k)-FAM(l), which is contrary to expectations. Hence, it appears that similar levels of absorption may be achieved with mouthsprays according to the invention as compared to mouthsprays containing buffer.

These very high results for nicotine absorption of buffer free mouthsprays, approximately at the level of buffer-containing mouthsprays, ensures that effective alleviation of nicotine craving relief is obtained by administration of the inventive, liquid mouthspray formulation to the oral cavity.

Example 6

Preparation of Fast Disintegrating Tablet

In the present example six fast disintegrating tablets (FDT) with 1 mg nicotine are prepared with formulations as outlined in table 6. The fast disintegrating tablet is prepared with NBT (nicotine bitartrate dihydrate). Punch used: 7.00 mm, circular, shallow concave, D tooling. Tablet weight: 100.0 mg.

TABLE 6

Fast disintegrating tablet compositions. Amounts are given in mg.

| | FDT(a) | FDT(b) | FDT(c) | FDT(d) | FDT(e) | FDT(f) |
|---|---|---|---|---|---|---|
| NBT | 2.849 | 2.849 | 2.849 | 2.849 | 2.849 | 2.849 |
| Microcrystalline cellulose | — | — | — | 40.175 | 40.175 | 40.175 |
| Mannitol | 81.351 | 81.351 | 81.351 | 40.175 | 40.175 | 40.175 |
| Crospovidone | 5.0 | — | — | 5.0 | — | — |
| Croscarmellose Sodium | — | 5.0 | — | — | 5.0 | — |
| Sodium Starch Glycolate | — | — | 5.0 | — | — | 5.0 |
| Peppermint | 4.0 | 4.0 | 4.0 | 4.0 | 4.0 | 4.0 |
| Menthol | 0.4 | 0.4 | 0.4 | 0.4 | 0.4 | 0.4 |
| Sucralose | 0.4 | 0.4 | 0.4 | 0.4 | 0.4 | 0.4 |
| Sodium carbonate | 5.0 | 5.0 | 5.0 | 5.0 | 5.0 | 5.0 |
| Silicium dioxide | — | — | — | 1.0 | 1.0 | 1.0 |
| Magnesium stearate | 1.0 | 1.0 | 1.0 | 1.0 | 1.0 | 1.0 |
| Total | 100.0 | 100.0 | 100.0 | 100.0 | 100.0 | 100.0 |

FDT = Fast disintegrating tablet.

Raw materials are weighed from bags or buckets into separate weighing containers.

All excipients are sifted through an 800 micrometer sieve into a stainless steel or plastic bin in the following order:
   Half the filler/bulk sweetener
   The API and all other excipients, except magnesium stearate
   The remaining half of the filler/bulk sweetener
These are mixed in a Turbula mixer for 4-10 minutes at 25 RPM. Then lubricant, for example magnesium stearate is sifted through an 800 micrometer sieve into the mixing bin, and the lubrication is conducted by additional mixing for 1-2 minutes at 25 RPM. The fill level of the mixing bin is kept between 40% and 70%, according to standardized practice. The lubricated powder blend is transferred to the hopper of a tableting machine.

The fast disintegrating tablets are manufactured on a lab scale machine, for example RIVA Piccola bi-layer tablet press. The tablet machine is commissioned by adjusting the fill depth and compression force so the weight and hardness of lozenges match the acceptance criteria. A pre-compression force could be included to avoid capping.

TABLE 7

Suggested start up parameters.

| Parameter | Target value |
|---|---|
| Speed | 10-20 rpm |
| Weight of FDT | 100 mg +/− 5% |
| Compression force | 2-8 kN |
| Thickness | N/A* |
| Friability (100 rpm) | <1% |

*The design of punches is not fixed. As the curvature impacts thickness, the thickness is not a fixed target at this time of development.

The acceptance criteria for friability should be fulfilled so packaging of the resulting fast disintegrating tablets is possible, but in this embodiment, the bulk sweetener and or filler should have relatively good compressibility and still have fast disintegration. The fast disintegrating tablets according to the invention may comprise coloring agents. According to an embodiment of the invention, the fast disintegrating tablets may comprise color agents and whiteners such as FD&C-type dyes and lakes, fruit and vegetable extracts, titanium dioxide and combinations thereof.

Example 7

Preparation of Fast Disintegrating Tablet Using Ready to Use Systems

Another way of preparing fast disintegrating tablets would be to use a ready to use system. Suitable for the purpose could be but not limited to: Pearlitol Flash (Roquette), Pharmaburst 500 (SPI Pharma), Ludiflash (BASF), ProSolv (JRS Pharma), ProSolv EasyTab (JRS Pharma), F-Melt (Fuji Chemical), SmartEx50 or SmartEx100 (Shin Etsu/Harke Pharma). These ready to use systems co-processed systems where filler, disintegrant, glidant or similar are implemented in the one powder mix. This saves handling of several excipients and ensures homogeneity between excipients.

In the present example five fast disintegrating tablets (FDT(g)-FDT(k)) without nicotine are prepared with ready to use systems in formulations as outlined in table 8A. The fast disintegrating tablet is prepared without NBT (placebo). Adding nicotine to the fast disintegrating tablets is expected to influence disintegration time only insignificantly.

In this example, the following conditions where applied. Punch used: 7.00 mm, circular, shallow concave, B tooling. Tablet weight: 100.0 mg.

Additionally, five fast disintegrating tables (FDT(l)-FDT(p)) with nicotine are prepared with ready to use systems in formulations as outlined in table 8B.

Further four fast disintegrating tablets (FDT(1)-FDT(4)) with nicotine are prepared with varying amounts of MCC as filler, as outlined in table 8C.

Also, four fast disintegrating tablets, FDT(5)-FDT(8), with nicotine are prepared with varying amounts of disintegrant, as outlined in table 8D.

Three fast disintegrating tablets, FDT(9)-FDT(11), with nicotine are prepared with varying amounts types of lubricants, as outlined in table 8E.

TABLE 8A

Fast disintegrating tablet compositions with different ready to use systems.

|  | FDT(g) | FDT(h) | FDT(i) | FDT(j) | FDT(k) |
|---|---|---|---|---|---|
| Ludiflash | 81.7 | — | — | — | — |
| Pearlitol Flash | — | 81.7 | — | — | — |
| SmartEx QD50 | — | — | 81.7 | — | — |
| F-Melt | — | — | — | 83.7 | — |
| ProSolv ODT G2 | — | — | — | — | 83.7 |
| Peppermint | 4.4 | 4.4 | 4.4 | 4.4 | 4.4 |
| Menthol | 1.5 | 1.5 | 1.5 | 1.5 | 1.5 |
| Sucralose | 0.4 | 0.4 | 0.4 | 0.4 | 0.4 |
| Sodium carbonate | 5.0 | 5.0 | 5.0 | 5.0 | 5.0 |
| Crospovidone | 5.0 | 5.0 | 5.0 | — | — |
| Croscarmellose Sodium | — | — | — | 3.0 | — |
| Sodium Starch Glycolate | — | — | — | — | 3.0 |
| Magnesium stearate | 2.0 | 2.0 | 2.0 | 2.0 | 2.0 |
| Total | 100.0 | 100.0 | 100.0 | 100.0 | 100.0 |

Amounts are given in mg.
FDT = Fast disintegrating tablet.

Additionally, five fast disintegrating tables (FDT(l)-FDT(p)) with nicotine are prepared with ready to use systems in formulations as outlined in table 8B.

In this example, the following conditions where applied. Punch used: 7.00 mm, circular, shallow concave, B tooling. Tablet weight: 100.0 mg.

TABLE 8B

Fast disintegrating tablet compositions with different ready to use systems and nicotine as nicotine bitartrate, NBT or nicotinepolacrilex, NPR (15% nicotine load).

|  | FDT(l) | FDT(m) | FDT(n) | FDT(o) | FDT(p) |
|---|---|---|---|---|---|
| NBT | — | — | 3.0 | 3.0 | 3.0 |
| NPR | 6.7 | 6.7 | — | — | — |
| Ludiflash | 75.0 | — | — | — | — |
| Pearlitol Flash | — | 75.0 | — | — | — |
| SmartEx QD50 | — | — | 78.7 | — | — |
| F-Melt | — | — | — | 80.7 | — |
| ProSolv ODT G2 | — | — | — | — | 80.7 |
| Peppermint | 4.4 | 4.4 | 4.4 | 4.4 | 4.4 |
| Menthol | 1.5 | 1.5 | 1.5 | 1.5 | 1.5 |
| Sucralose | 0.4 | 0.4 | 0.4 | 0.4 | 0.4 |
| Sodium carbonate | 5.0 | 5.0 | 5.0 | 5.0 | 5.0 |
| Crospovidone | 5.0 | 5.0 | 5.0 | — | — |
| Croscarmellose Sodium | — | — | — | 3.0 | — |
| Sodium Starch Glycolate | — | — | — | — | 3.0 |
| Magnesium stearate | 2.0 | 2.0 | 2.0 | 2.0 | 2.0 |
| Total | 100.0 | 100.0 | 100.0 | 100.0 | 100.0 |

Amounts are given in mg.
FDT = Fast disintegrating tablet.

Further four fast disintegrating tablets (FDT(1)-FDT(4)) with nicotine are prepared with varying amounts of MCC (microcrystalline cellulose) as filler, as outlined in table 8C.

In this example, the following conditions where applied. Punch used: 7.00 mm, circular, shallow concave, B tooling. Tablet weight: 100.0 mg.

TABLE 8C

Fast disintegrating tablet compositions with varying amounts of MCC and nicotine (1 mg/tablet) sorbed onto calcium carbonate (synthetic free nicotine base sorbed onto calcium carbonate in a weight ratio of 1:2).

|  | FDT(1) | FDT(2) | FDT(3) | FDT(4) |
|---|---|---|---|---|
| Nicotine-calcium carbonate | 3.0 | 3.0 | 3.0 | 3.0 |
| Microcrystalline cellulose | 0.0 | 5.0 | 10.0 | 20.0 |
| Mannitol | 79.7 | 74.7 | 69.7 | 59.7 |
| Crospovidone | 5.0 | 5.0 | 5.0 | 5.0 |
| Peppermint | 4.4 | 4.4 | 4.4 | 4.4 |
| Menthol | 1.5 | 1.5 | 1.5 | 1.5 |
| Sucralose | 0.4 | 0.4 | 0.4 | 0.4 |
| Sodium carbonate | 5.0 | 5.0 | 5.0 | 5.0 |
| Magnesium stearate | 1.0 | 1.0 | 1.0 | 1.0 |
| Total | 100.0 | 100.0 | 100.0 | 100.0 |

Amounts are given in mg.
FDT = Fast disintegrating tablet.

Also, four fast disintegrating tablets, FDT(5)-FDT(8), with nicotine are prepared with varying amounts of disintegrant, as outlined in table 8D.

In this example, the following conditions where applied. Punch used: 7.00 mm, circular, shallow concave, B tooling. Tablet weight: 100.0 mg.

TABLE 8D

Fast disintegrating tablet compositions with varying amount of disintegrant.

|  | FDT(5) | FDT(6) | FDT(7) | FDT(8) |
|---|---|---|---|---|
| NBT | 3.0 | 3.0 | 3.0 | 3.0 |
| Mannitol | 41.7 | 39.2 | 41.7 | 31.7 |
| Microcrystalline cellulose | 43 | 43 | 43 | 43 |
| Crospovidone | 0.0 | 2.5 | 5.0- | 10.0 |
| Peppermint | 4.4 | 4.4 | 4.4 | 4.4 |
| Menthol | 1.5 | 1.5 | 1.5 | 1.5 |
| Sucralose | 0.4 | 0.4 | 0.4 | 0.4 |

TABLE 8D-continued

Fast disintegrating tablet compositions with varying amount of disintegrant.

|  | FDT(5) | FDT(6) | FDT(7) | FDT(8) |
|---|---|---|---|---|
| Sodium carbonate | 5.0 | 5.0 | 5.0 | 5.0 |
| Magnesium stearate | 1.0 | 1.0 | 1.0 | 1.0 |
| Total | 100.0 | 100.0 | 100.0 | 100.0 |

Amounts are given in mg.
FDT = Fast disintegrating tablet.

Three fast disintegrating tablets, FDT(9)-FDT(11), with nicotine are prepared with varying types of lubricants, as outlined in table 8E.

In this example, the following conditions where applied.
Punch used: 7.00 mm, circular, shallow concave, B tooling.
Tablet weight: 100.0 mg.

TABLE 8E

Fast disintegrating tablet compositions.

|  | FDT(9) | FDT(10) | FDT(11) |
|---|---|---|---|
| NBT | 3.0 | 3.0 | 3.0 |
| Microcrystalline cellulose | 5 | 5 | 5 |
| Mannitol | 78.6 | 77.6 | 77.6 |
| Crospovidone | 5.0 | 5.0 | 5.0 |
| Eucamenthol Flavour | 2 | 2 | 2 |
| Sucralose | 0.4 | 0.4 | 0.4 |
| Sodium carbonate | 5.0 | 5.0 | 5.0 |
| Magnesium stearate | 1.0 | — | — |
| Sodium stearyl fumarate | — | 2.0 | — |
| Compritol HD5 | — | — | 2.0 |
| Total | 100.0 | 100.0 | 100.0 |

Amounts are given in mg.
FDT = Fast disintegrating tablet.

Three fast disintegrating tablets, FDT(12)-FDT(14) as outlined in table 8F.

In this example, the following conditions where applied.
Punch used: 7.00 mm, circular, shallow concave, B tooling.
Tablet weight: 75.0 mg.

TABLE 8F

Fast disintegrating tablet compositions.

|  | FDT(12) | FDT(13) | FDT(14) |
|---|---|---|---|
| SmartEx QD 50 | 60.0 | 65.0 | 65.0 |
| Nicotine Bitartrate (NBT) | 3.0 | 3.0 | 3.0 |
| Sodium carbonate anhydrous | 5.0 | 0.0 | 5.0 |
| Crospovidone (Kollidon CL-F, BASF) | 5.0 | 5.0 | 0.0 |
| Peppermint Powder | 0.4 | 0.4 | 0.4 |
| Sucralose | 0.4 | 0.4 | 0.4 |
| Aerosil 200 (silicium dioxide) | 0.2 | 0.2 | 0.2 |
| Magnesium Stearate | 1.0 | 1.0 | 1.0 |
| Total | 75.0 | 75.0 | 75.0 |

Amounts are given in mg.
FDT = Fast disintegrating tablet.
FDT(13) was made similar to FDT(12) but without buffer.
FDT(14) was made similar to FDT(12) but without disintegrant.

FDT(12)-FDT(13) were pressed to a hardness of 15-20 N.
FDT (14) was pressed to a hardness of 25-35 N.

An oral pouch is prepared comprising a powdered composition, PPC 1, as outlined in table 8G. The pouch is made as follows.

The nicotine-resin complex used herein is made by mixing water, nicotine, resin (Amberlite® IRP64) and glycerin. When a homogeneous solution is obtained and all nicotine has been bound by the ion exchange resin the pressure is reduced and the obtained mixture is concentrated in vacuum at elevated temperature affording the desired complex as a powder. The nicotine-resin complex is sieved.

Any cationic ion exchange resin complex (preferable a non-ionic pharmaceutical grade resin) may in principle be used. The resin is capable of binding anionic molecules at the ion exchange sites.

The obtained nicotine-resin complex powder is mixed using a Turbula mixer for 6 minutes (speed 49 rpm) with the remaining ingredients to obtain a final powder composition.

The final powder composition is filled into pouches (target fill weight 400 mg powder per pouch). The following pouch, made from long fiber paper, is used.

The material of the pouches is heat sealable non-woven cellulose, such as long fiber paper. Pouches that are not in form of non-woven cellulose fabric may also be used according to the invention.

The powder is filled into pouches and is maintained in the pouch by a sealing.

When including smaller amounts of further humectants, apart from e.g. sugar alcohols, these further humectants are added in the same manner as magnesium stearate.

TABLE 8G

Nicotine pouch; NPR is nicotine polacrilex resin where the resin is Amberlite ™ IRP64.

| Raw material | PPC 1<br>Amount of nicotine<br>3 mg<br>Content in weight percent |
|---|---|
| NPR | 4.75 |
| Isomalt GalenIQ 720 | 45 |
| Zerose TM erythritol | 40 |
| Sodium carbonate | 2.50 |
| Sodium bicarbonate | 4.00 |
| Flavor | 3.60 |
| Acesulfame potassium | 0.15 |
| Total | 100 |

Pouches contain 400 mg per piece.

Preparation of fast dissolving pouches with residue containing nicotine polacrilex resin (NPR) or nicotine bitartrate (NBT) are prepared comprising powdered compositions, PPC 2-7, as outlined in table 8H.

Preparation of fast dissolving pouches without residue containing nicotine polacrilex resin (NPR) or nicotine bitartrate (NBT) are prepared comprising powdered compositions, PPC 8-13, as outlined in table 8I.

The pouches are made as follows.

For PPC 6, and 8-10 a method corresponding to that used for PPC 1 was used.

For PPC 2-5, 7 and 11-13, the below method was used.

Nicotine bitartrate xH2O is mixed using a Turbula mixer for 6 minutes (speed 49 rpm) with the remaining ingredients to obtain a final powder composition.

The final powder composition is filled into pouches (target fill weight 400 mg powder per pouch). The pouch material of example 2, made from long fiber paper, is used. The powder is filled into pouches and is maintained in the pouch by a sealing.

The material of the pouches is heat sealable non-woven cellulose, such as long fiber paper. Pouches that are not in form of non-woven cellulose fabric may also be used according to the invention.

The powder is filled into pouches and is maintained in the pouch by a sealing.

When including smaller amounts of further humectants, apart from e.g. sugar alcohols, these further humectants are added in the same manner as magnesium stearate.

When further adding magnesium stearate, this may be added by full powder mixture during the last few minutes of the final mixing.

As described below, the tablets according to the invention may be made from a wide range of different formulations.

As can be seen in table 6, microcrystalline cellulose is used as a filler. Lower amount of filler such as microcrystalline cellulose may also be used. Examples of usable fillers include magnesium- and calcium carbonate, sodium sul-

TABLE 8H

Nicotine pouch; NPR is nicotine polacrilex resin where the resin is Amberlite ™ IRP64.

| | PPC | | | | | |
|---|---|---|---|---|---|---|
| | 2 | 3 | 4 | 5 | 6 | 7 |
| | | | Amount of nicotine | | | |
| Raw material | 3 mg | 3 mg | 3 mg | 3 mg | 3 mg | 3 mg |
| | | | Content in weight percent | | | |
| NPR | — | — | — | — | 4.75 | — |
| NBT | 2.14 | 2.14 | 2.14 | 2.14 | — | 2.14 |
| Isomalt GalenIQ 720 | 67.7 | — | 67.7 | — | 62.6 | 67.7 |
| Maltitol SweetPearl 300 DC | — | 67.7 | — | 65.2 | — | — |
| Sodium carbonate | 2.50 | 2.50 | 2.50 | 2.50 | 2.50 | 2.50 |
| Sodium bicarbonate | 4.00 | 4.00 | 4.00 | 4.00 | 4.00 | 4.00 |
| Peppermint flavor | 2.50 | 2.50 | 2.50 | 2.50 | 2.50 | — |
| Menthol | 1.00 | 1.00 | 1.00 | — | — | — |
| Eucalyptos flavor | — | — | — | 3.50 | 3.50 | 3.50 |
| Acesulfame potassium | 0.16 | 0.16 | 0.16 | 0.16 | 0.15 | 0.16 |
| Dibasic Calcium Phosphate anhydr. | 20.00 | 20.00 | — | — | — | — |
| Calcium carbonate DC | — | — | 20.00 | 20.00 | — | — |
| Mono-, diglyceride powder (emulsifier) | — | — | — | — | 10.00 | 10.00 |
| Hydrogenated Vegetable oil (solid state) | — | — | — | — | 10.00 | 10.00 |
| Total | 100 | 100 | 100 | 100 | 100 | 100 |

NBT is nicotine bitartrate.
Pouches contain 400 mg per piece.

TABLE 8I

Nicotine pouch; NPR is nicotine polacrilex resin where the resin is Amberlite ™ IRP64.

| | PPC | | | | | |
|---|---|---|---|---|---|---|
| | 8 | 9 | 10 | 11 | 12 | 13 |
| | | | Amount of nicotine | | | |
| Raw material | 3 mg | 3 mg | 3 mg | 3 mg | 3 mg | 3 mg |
| | | | Content in weight percent | | | |
| NPR | 4.75 | 4.75 | 4.75 | — | — | — |
| NBT | — | — | — | 2.14 | 2.14 | 2.14 |
| Isomalt GalenIQ 720 | — | 85.1 | — | — | 87.7 | — |
| Zerose TM erythritol | 85.1 | — | — | 87.7 | — | — |
| Maltitol SweetPearl 300 DC | — | — | 85.1 | — | — | 87.7 |
| Sodium carbonate and. | 2.50 | 2.50 | — | — | — | 2.50 |
| Sodium bicarbonate | 4.00 | 4.00 | — | — | — | 4.00 |
| Effersoda | — | — | 6.50 | 6.50 | 6.50 | — |
| Peppermint flavor | 2.50 | 2.50 | 2.50 | — | — | — |
| Menthol | 1.00 | 1.00 | 1.00 | — | — | — |
| Eucalyptos flavor | — | — | — | 3.50 | 3.50 | 3.50 |
| Acesulfame potassium | 0.15 | 0.15 | 0.15 | 0.16 | 0.16 | 0.16 |
| Total | 100 | 100 | 100 | 100 | 100 | 100 |

NBT is nicotine bitartrate.
Pouches contain 400 mg per piece.

phate, ground limestone, silicate compounds such as magnesium- and aluminum silicate, kaolin and clay, aluminum oxide, silicium oxide, talc, titanium oxide, mono-, di- and tri-calcium phosphates, cellulose polymers, such as wood, starch polymers, fibers and combinations thereof.

As can be seen in table 6, mannitol is used as a bulk sweetener. Examples of usable bulk sweeteners include sugar sweetener and/or sugarless sweetener.

The bulk sweeteners may often support the flavor profile of the formulation.

Sugarless sweeteners generally include, but are not limited to sugar alcohols (also sometimes referred to as polyols) such as sorbitol, erythritol, xylitol, maltitol, mannitol, lactitol, and isomalt.

Sugar sweeteners generally include, but are not limited to saccharide-containing components, such as sucrose, dextrose, maltose, saccharose, lactose, sorbose, dextrin, trehalose, D-tagatose, dried invert sugar, fructose, levulose, galactose, corn syrup solids, glucose syrup, hydrogenated glucose syrup, and the like, alone or in combination. These sugar sweeteners may also be included as a humectant.

As can be seen in table 6 and 8A-8F, crospovidone, croscarmellose sodium, and sodium starch glycolate are used as disintegrants in fast disintegrating tablets. Examples of usable disintegrants include starch, pregelatinated starch, modified starch (including potato starch, maize starch, starch 1500, sodium starch glycolate and starch derivatives), cellulose, microcrystalline cellulose, alginates, ion-exchange resin, and superdisintegrants, such as crosslinked cellulose (such as sodium carboxy methyl cellulose), crosslinked polyvinyl pyrrolidone (PVP), crosslinked starch, crosslinked alginic acid, natural superdisintegrants, and calcium silicate, and combinations thereof.

As can be seen in table 6 and 8A-8G, sucralose is used as a high intensity sweetener. Usable high intensity sweeteners include, but are not limited to sucralose, aspartame, salts of acesulfame, such as acesulfame potassium, alitame, saccharin and its salts, cyclamic acid and its salts, glycyrrhizin, dihydrochalcones, thaumatin, monellin, stevioside and the like, alone or in combination.

As can be seen in table 6 and 8A-8G, peppermint and menthol are used as flavors. Usable flavors include almond, almond amaretto, apple, Bavarian cream, black cherry, black sesame seed, blueberry, brown sugar, bubblegum, butterscotch, cappuccino, caramel, caramel cappuccino, cheesecake (graham crust), cinnamon redhots, cotton candy, circus cotton candy, clove, coconut, coffee, clear coffee, double chocolate, energy cow, graham cracker, grape juice, green apple, Hawaiian punch, honey, Jamaican rum, Kentucky bourbon, kiwi, koolada, lemon, lemon lime, tobacco, maple syrup, maraschino cherry, marshmallow, menthol, milk chocolate, mocha, Mountain Dew, peanut butter, pecan, peppermint, raspberry, banana, ripe banana, root beer, RY 4, spearmint, strawberry, sweet cream, sweet tarts, sweetener, toasted almond, tobacco, tobacco blend, vanilla bean ice cream, vanilla cupcake, vanilla swirl, vanillin, waffle, Belgian waffle, watermelon, whipped cream, white chocolate, wintergreen, amaretto, banana cream, black walnut, blackberry, butter, butter rum, cherry, chocolate hazelnut, cinnamon roll, cola, creme de menthe, eggnog, English toffee, guava, lemonade, licorice, maple, mint chocolate chip, orange cream, peach, pina colada, pineapple, plum, pomegranate, pralines and cream, red licorice, salt water taffy, strawberry banana, strawberry kiwi, tropical punch, tutti frutti, vanilla, or any combination thereof.

According to an embodiment of the invention, flavor may be used as taste masking for the nicotine.

In some embodiments of the invention, the formulation comprises pH regulating agent.

In some embodiments of the invention, the formulation comprises pH regulating agent in an amount of 2.7 to 5.7% by weight of said formulation.

In some embodiments of the invention, the pH regulating agent comprises buffer.

As can be seen in table 6 and 8A-8G, sodium carbonate is used as a buffering agent. Usable buffering agents include carbonate, including monocarbonate, bicarbonate and sesquicarbonate, glycerinate, phosphate, glycerophosphate, acetate, gluconate or citrate of an alkali metal, ammonium, tris buffer, amino acids and mixtures thereof. Encapsulated buffer such as Effersoda may also be used.

In some embodiments, the formulation comprises buffering agent in an amount of from 2.7 to 5.7% by weight of the formulation.

The buffering agent may be added to the formulation together with the water-soluble fast disintegrating tablet ingredients.

When buffering agent is added to the fast disintegrating tablet as part of the water-soluble fast disintegrating tablet ingredients, a pH-profile according to embodiments of the present invention can be obtained.

Buffering agent in the tablet may be used to obtain the desired pH-values in the saliva of a tablet user.

In some embodiments, the buffering agent comprises sodium carbonate and sodium bicarbonate, e.g. in a weight-ratio between 5:1 and 2.5:1, preferably in a weight-ratio between 4.1:1 and 3.5:1.

A high suitable buffering agent according to advantageous embodiments of the present invention is the sodium carbonate-sodium bicarbonate buffer system.

As can be seen in table 6, silicon dioxide is used as a glidant. Other glidants usable for the formulation may also be used within the scope of the invention.

As can be seen in table 6 and 8A-8G, magnesium stearate is used as a lubricant. Other lubricants usable for the formulation may also be used within the scope of the invention.

As can be seen in table 8A-8F, ready to use systems may be used for preparation of tablets. Typically, such ready-to-use systems may e.g. replace filler, disintegrant, glidant or similar with a single powder mix. Suitable ready-to-use systems for the purpose, but not limited to, include Pearlitol Flash (Roquette), Pharmaburst 500 (SPI Pharma), Ludiflash (BASF), ProSolv (JRS Pharma), ProSolv EasyTab (JRS Pharma), F-Melt (Fuji Chemical), SmartEx50 or SmartEx100 (Shin Etsu/Harke Pharma).

In order to obtain a formulation providing a peak saliva concentration of nicotine of more than 0.3 mg/mL, such as more than 0.5 mg/mL, and a peak saliva pH of more than 7.5 during the first 120 seconds upon oral administration a range of parameters can be adjusted.

First of all, whether the formulation is solid or liquid, having a higher dosage of nicotine and pH regulating agent supports obtaining the high peak saliva concentration of nicotine and the high peak saliva pH of the invention. Thus, if a given product provides a too low peak nicotine concentration, the nicotine dosage may be increased until the desired peak nicotine concentration is obtained, possibly together with other suitable modifications. Increasing the dosage may be obtained by increasing the nicotine concentration. For e.g. tablets and pouches, the total amount of formulation provided in a tablet or pouch may also be increased.

Moreover, the used nicotine form may be varied in order reduce the dissolving time of nicotine, when nicotine needs to be dissolved. For example, nicotine salts are typically relatively fast dissolving. An example of a fast dissolving nicotine salt is nicotine bitartrate. Other nicotine salts described herein are also usable within the scope of the invention.

When solid powders are used as the dosage form, the particle size of the powder may also be adjusted to influence dissolution time, which again facilitates obtaining the high peak saliva concentration and high peak saliva pH. A smaller particle size decreases the dissolution time.

Furthermore, if the formulation is provided as a solid formulation, such as e.g. a tablet or a powder, an important parameter is the disintegration time. For example, obtaining a fast disintegration, such as a disintegration of the formulation within 60 seconds upon oral administration facilitates the high peak saliva concentration of nicotine and the high peak saliva pH of the invention.

Concerning the peak saliva pH, it is noted that increasing the strength, the amount, and the concentration of the pH regulating agent are examples of relevant parameters that may be adjusted to obtain a higher peak saliva pH.

In order to obtain a fast disintegrating tablet, such as a tablet being designed for disintegrating within a period of 60 second upon oral administration, a range of parameters can be adjusted.

First, by varying the composition, the disintegration time can be altered. Using ingredients with a high water-solubility may facilitate a lowered disintegration time.

Particularly, including a disintegrant may significantly influence the disintegration time, subject to the total composition. Also, by varying the amount and type of the disintegrant, the disintegration time may be further adjusted. For example, if a tablet having a lower disintegration time is desired, the percentage content of disintegrant may be increased and/or the type of disintegrant may be at least partly exchanged for a more effective disintegrant.

Also, decreasing the particle size of the disintegrant tends to lower the disintegration time, likely due to an increased surface area to volume ratio.

Furthermore, the compression force used in compressed tablets correlate significantly with the obtained hardness, such that a high compression force typically increases the hardness of the obtained tablet. By adjusting the hardness of a tablet, the disintegration time may also be influenced, such that a lowered hardness typically gives a shorter disintegration time. Here it has been observed for a number of compositions that by applying the correct compression force a disintegration time below 60 second upon oral administration can be achieved, whereas a too high compression force may result in a longer disintegration time above 60 seconds. In this regard it is noted that the threshold compression force may vary significantly, depending on other parameters, such as overall composition, content and type of disintegrant, etc. When, for example, a certain setup results in a too slow disintegration, a further way of adjusting may be to replace a regular disintegrant with a superdisintegrant, i.e. which facilitates disingration in a more efficient way.

For solid formulations, increasing the water-solubility may also be facilitated by exchanging ingredients with low water-solubility with ingredients having higher water-solubility. For example, using sugar alcohols as fillers may be very advantageous insofar that the sugar alcohols have a higher water solubility than alternative fillers.

Moreover, using sugar alcohols with a lower compactibility leads to lower disintegration time. For tablets, too low compactibility may compromise the mechanical strength of the tablet and lead to undesirably high friability and risk of cracks etc.

Further examples of parameters that may be adjusted in order to obtain a fast disintegrating formulation, such as a formulation being designed for disintegrating within a period of 60 second upon oral administration include size and shape of the tablet when a tablet is used as the dosage form. The larger the tablet, the longer the disintegration time and thus release time of the nicotine and pH regulating agent.

For example, increasing the flatness (e.g. quantified by a diameter to height ratio) for a disc-shaped tablet typically increases disintegration time by increasing the surface-to-volume. As long as the tablet has a satisfactory mechanical strength, flatness may be increased.

Also, modifying the cross-sectional profile from a convex type tablet to a concave shaped tablet lowers the disintegration time. It is noted that this may to some degree lower the mechanical strength of the tablet, however, as long as it is satisfactory, pursuing the concave cross-section may help to increase disintegration and thus lower the disintegration time.

Also, when using binders in solid formulations such as tablets or powders, e.g. to obtain a higher cohesiveness and mechanical strength of the tablet, the amount of such binders may be decreased as much as possible to obtain a higher disintegration rate and thus a shorter disintegration time.

Furthermore, by adding a salivation agent to the solid formulation, an increased amount of saliva in the vicinity of the formulation may be facilitated, which again supports the dissolving and disintegration of the formulation to reduce the disintegration time.

A further important parameter for liquid and solid formulations is any encapsulation of nicotine and/or the pH regulating agent. While encapsulation may in some embodiments be allowable, such encapsulation leads to a slower release. Therefore, it the desired high peak saliva concentration of nicotine and the high peak saliva pH of the invention is not obtained, any encapsulation may be decreased or dispensed with in order to obtain the desired results.

In general, for a given dosage form, the peak saliva concentration of nicotine and the peak saliva pH may be measured. If the desired values are not obtained, the above described parameters may be adjusted as instructed herein. This allows the desired values to be obtained using a minimum of experimentation.

Further, the type and amount of lubricant, if any, may be adjusted to optimize disintegration time. For example, using Sodium stearyl fumarate (SSF) typically leads to a lower disintegration time compared to when using magnesium stearate MgSt.

Thus, a wide range of parameters may be adjusted when designing a formulation designed to provide a peak saliva concentration of nicotine of more than 0.3 mg/mL, such as more than 0.5 mg/mL, and a peak saliva pH of more than 7.5 during the first 120 seconds upon oral administration.

Typically, the solid formulation comprises of ingredients selected from the group consisting of bulk sweeteners, fillers, ready to use systems, flavors, dry-binders, disintegrant, hereunder superdisintegrants, tabletting aids, anti-caking agents, emulsifiers, antioxidants, enhancers, absorption enhancers, buffering agents, high intensity sweeteners, colors, glidants, lubricants, or any combination thereof. Here, tabletting aids are used for tablets but not for other powder formulations. Absorption enhancers may include e.g. pH regulating agents, such as buffering agents, and mucoadhesive.

In an embodiment of the invention, the tablet core is provided with an outer coating.

In an embodiment of the invention, said outer coating is selected from the group consisting of hard coating, soft coating and edible film-coating or any combination thereof.

According to an embodiment of the invention, at least a part of the nicotine is adhered to dry-binder particles.

According to an embodiment of the invention, an amount of dry-binder is used to adhere nicotine to bulk sweetener.

According to an embodiment of the invention, said fast disintegrating tablet comprises one or more encapsulation delivery systems.

Example 8

In Vivo pH

The fast disintegrating tablets are designed to have an in vivo pH higher than the resting saliva pH in the mouth. Thus, pH is measured in vivo, as follows:

At least 6 individuals chewed on a gum base free of buffer for 1 minute, after which the initial pH in a sample from the saliva from each of the individuals is measured with a suitable pH-electrode system, e.g. a stainless-steel electrode PHW77-SS. Only individuals having, after chewing on a gum base free of buffer for one minute, an initial pH in the saliva inside the range from 6.7 and 7.3 are selected. These individuals thereby qualify as average individuals.

One tablet is administered sublingually to at least six individuals. Hereafter, the saliva pH from each of the six individuals is measured at specified time intervals. Thus, each pH-value is the arithmetic mean of six measurements performed on saliva-samples from six individuals.

The sample volume of the individual saliva-samples may vary because the volume of saliva obtained may be different from each individual. This difference in sample volume does not affect the pH-measurements significantly. Also, it has been established by appropriate tests that a variation in time between collections of samples does not significantly alter the result. This means that the measured pH-value after three minutes is not significantly affected by whether another saliva-sample is taken from the six individuals e.g. after two minutes or not. Furthermore, it has been established by appropriate tests that the time from taking a sample to the time of measuring is not critical to the measured value. However, in the present measurements, the pH-values were measured in the samples within at most 15 minutes of sample collection.

The results are shown in table 8J.

TABLE 8J

In vivo pH. Nicorette Microtab (2 mg), Nicotinell Mint Lozenge (2 mg), and Nicotinell Mint Chewing gum (2 mg) were commercially available products.

| | pH | | | In vivo DT |
|---|---|---|---|---|
| | 10 sec | 20 sec | 90 sec | (sec) |
| FDT (12) (1 mg) | 9.3 | 9.1 | 8.4 | 20 |
| FDT (14) (1 mg) | 7.4 | 7.2 | 7.6 | 210 |
| FDT (13) (1 mg) | 5.3 | 5.8 | 6.5 | 15 |
| Nicorette Microtab (2 mg) | 6.7 | 6.8 | 6.8 | >600 |

TABLE 8J-continued

In vivo pH. Nicorette Microtab (2 mg), Nicotinell Mint Lozenge (2 mg), and Nicotinell Mint Chewing gum (2 mg) were commercially available products.

| | pH | | | In vivo DT |
|---|---|---|---|---|
| | 10 sec | 20 sec | 90 sec | (sec) |
| Nicotinell Mint Lozenge (2 mg) | 6.9 | 7.1 | 7.2 | >600 |
| Nicotinell Mint Chewing gum (2 mg) | 7.2 | 7.4 | 7.6 | NA |

As can be seen from table 8G, the pH exceeds 7.5 for FDT 12 and 13. For FDT 12, this even applies already at 10 and 20 seconds from contact with oral saliva. FDT(13), made without any buffer, did not give a pH above 7.5.

The needed raise in saliva pH is at least 0.5-1.0 pH units. A conventional nicotine mouth spray was chosen for comparison as well as Nicorette Microtab, Nicotinell Mint Lozenge, and Nicotinell Mint chewing gum. The conventional nicotine mouth spray reveals also fast craving relief. The conventional nicotine mouth spray raises the pH in saliva up to a maximum of 8.5 according to internal measurements. None of Nicorette Microtab and Nicotinell Mint Lozenge resulted in pH above 7.2. Nicotinell Mint chewing gum did not result in pH above 7.6.

The sample volume of the individual saliva-samples may vary because the volume of saliva obtained may be different from each individual. This difference in sample volume does not affect the pH-measurements significantly.

It should be noted that the in vivo pH would be different from an in vitro pH due to the fact that acidic sodium bicarbonate is normally continuously produced in saliva, hence neutralizing the alkaline contribution from buffer. Thus, the pH obtained in vivo will be lower than in vitro measured by e.g. dissolving the tablet in a beaker.

Example 9

Disintegration of Nicotine Tablets

The in vitro disintegration of the fast disintegrating tablets of example 6 and 7 was carried out in accordance to European Pharmacopeia 9.0, section 2.9.1, Disintegration of tablets and capsules. As described in the examples each batch has been manufactured in various tablet sub lots where the compression force has been varied and therefore the output parameters like hardness and friability will also vary. These output parameters do also have an impact on in vitro disintegration. The results for example 6 are outlined in table 9. A minimum and a maximum value for measured disintegration are given and this is more or less a function of the hardness.

TABLE 9

In vitro disintegration, hardness, friability. Time is given in seconds.

| | Mean in vitro disintegration (sec) | | Mean hardness (N) | | Mean friability (%) | |
|---|---|---|---|---|---|---|
| | Min (sec) | Max (sec) | Min (N) | Max (N) | Min (%) | Max (%) |
| FDT(a) | 21 | 24 | 14 | 63 | 0.0 | 0.3 |
| FDT(b) | 23 | 98 | 12 | 50 | 0.0 | 0.6 |

TABLE 9-continued

In vitro disintegration, hardness, friability.
Time is given in seconds.

|  | Mean in vitro disintegration (sec) | | Mean hardness (N) | | Mean friability (%) | |
| --- | --- | --- | --- | --- | --- | --- |
|  | Min (sec) | Max (sec) | Min (N) | Max (N) | Min (%) | Max (%) |
| FDT(c) | 29 | 177 | 14 | 55 | 0.0 | 0.5 |
| FDT(d) | 15 | 177 | 19 | 62 | 0.0 | 0.0 |
| FDT(e) | 13 | 175 | 15 | 45 | 0.0 | 0.2 |
| FDT(f) | 11 | 259 | 14 | 43 | 0.0 | 0.2 |

The above table should be interpreted as illustrated in the following example. When looking at e.g. FDT(a), the minimum mean disintegration time of 21 seconds correspond to a tablet pressed just hard enough to obtain a cohesive tablet having a minimum mean hardness of 14 N and a friability of 0.3%. Similarly the maximum mean disintegration time of 24 seconds correspond to another tablet pressed harder to have a maximum mean hardness of 63 N. In this way, the tablet having a mean friability of 0.0% of FDT(a) corresponds to the tablet having a mean hardness of 63 N. In other words, in table 9 FDT(a) refers to two different tablets pressed at two different pressures, the linking being indicated above. I.e. each line corresponds to two different tablets, one for Min values of disintegration time and hardness and the Max value for friability, and another for Max values of disintegration time and hardness and the Min value for friability.

The results for example 7 are outlined in table 10.

TABLE 10

In vitro disintegration, hardness, friability.
Time is given in seconds.

|  | Mean in vitro disintegration (sec) | | Mean hardness (N) | | Mean friability (%) | |
| --- | --- | --- | --- | --- | --- | --- |
|  | Min (sec) | Max (sec) | Min (N) | Max (N) | Min (%) | Max (%) |
| FDT(g) | 120 | 210 | 17 | 22 | N/A | 0.5 |
| FDT(h) | 40 | 80 | 16 | 24 | 0.5 | 0.8 |
| FDT(i) | 10 | 46 | 17 | 22 | 0.3 | 0.3 |
| FDT(j) | 42 | 150 | 17 | 22 | 0.7 | 1.0 |
| FDT(k) | 45 | 201 | 17 | 22 | 0.6 | 0.9 |

The above table should be interpreted as illustrated in the example below table 9.

It is seen that the in vitro disintegrating may vary a lot between the disclosed fast disintegrating tablets. Hereby a disintegration profile as desired may be used together with a high in vivo pH (as described in example 8), whereby the nicotine may be more efficiently used. Most preferable an in vitro disintegrating profile below 60 seconds is desired since it would ensure a high concentration of nicotine combined with relatively high in vivo pH.

The in vitro disintegration is a fast method to determine the time and mechanism for tablet performance. More preferable or in combination the in vivo disintegration is measured. The in vivo disintegration time is a value for the actual disintegration of the sublingual tablet under the tongue. Table 11 and 12 highlights the results for in vivo disintegration.

TABLE 11

In vivo disintegration.

|  | Mean in vivo disintegration (sec) | |
| --- | --- | --- |
|  | Min (sec) | Max (sec) |
| FDT(a) | 34 | 52 |
| FDT(b) | 18 | 27 |
| FDT(c) | 37 | N/A |
| FDT(d) | 42 | N/A |
| FDT(e) | 46 | N/A |

Time is given in seconds.

TABLE 12

In vivo disintegration.

|  | Mean in vivo disintegration (sec) | |
| --- | --- | --- |
|  | Min (sec) | Max (sec) |
| FDT(g) | 19 | 40 |
| FDT(h) | 13 | 48 |
| FDT(i) | 32 | 80 |
| FDT(j) | N/A | 56 |
| FDT(k) | N/A | 81 |

Time is given in seconds.

The above tables 11-12 should be interpreted as illustrated in the example below table 9.

As recognized for the in vitro disintegration results above the speed of in vivo disintegrating may be varied between the disclosed formulations. The disintegration time should be complete within 60 seconds from the onset of disintegration or preferable faster.

Since dissolution of nicotine bitartrate is a relatively fast process, the time used to release the content of nicotine can be taken as the disintegration time of the matrix (here the tablet).

Example 10

Nicotine Release and Absorption

Measurements of nicotine concentration are performed as follows:

One dose of the tablets of example 6 and 7 is administered sublingually to at least six individuals. At specified time intervals, the saliva is collected. The experiment is repeated. Thus, each nicotine concentration value is the arithmetic mean of 12 measurements, i.e. performed on saliva-samples from six individuals times 2. The nicotine concentration of saliva is analyzed on HPLC after extraction into relevant buffer.

Results are shown in tables 13A-13C.

TABLE 13A

Concentration of nicotine in saliva.

|  | Measuring time from initial contact with oral saliva [seconds] | | |
| --- | --- | --- | --- |
|  | 10 | 20 | 90 |
|  | Concentration of nicotine [mg/mL] | | |
| 2 mg Nicotinell Mint Lozenge | 0.06 | 0.05 | 0.10 |

TABLE 13A-continued

Concentration of nicotine in saliva.

| | Measuring time from initial contact with oral saliva [seconds] | | |
|---|---|---|---|
| | 10 | 20 | 90 |
| | Concentration of nicotine [mg/mL] | | |
| 1 mg FDT (12) | 0.52 | 0.59 | 0.52 |
| 1 mg FDT (13) | 0.74 | 0.66 | 0.66 |
| 1 mg FDT (14) | 0.36 | 0.39 | 0.33 |
| Nicorette Microtab 2 mg | 0.03 | 0.05 | 0.13 |
| Nicotinell Mint Chewing gum (2 mg) | 0.02 | 0.04 | 0.18 |

N/A = Not applicable (not assessed)

TABLE 13B

Concentration of nicotine in residue.

| | Measuring time from initial contact with oral saliva [seconds] | | |
|---|---|---|---|
| | 10 | 20 | 90 |
| | Concentration of nicotine [mg/mL] | | |
| 2 mg Nicotinell Mint Lozenge | 1.90 | 1.91 | 1.85 |
| 1 mg FDT (12) | No residue | No residue | No residue |
| 1 mg FDT (13) | No residue | No residue | No residue |
| 1 mg FDT (14) | N/A | N/A | No residue |
| Nicorette Microtab 2 mg | 1.90 | 1.87 | 1.77 |
| Nicotinell Mint Chewing gum (2 mg) | 1.98 | 1.96 | 1.72 |

N/A = Not applicable (not assessed)

TABLE 13C

Absoprtion of nicotine.

| | Measuring time from initial contact with oral saliva [seconds] | | |
|---|---|---|---|
| | 10 | 20 | 90 |
| | Absorption of nicotine [% by weight] | | |
| 2 mg Nicotinell Mint Lozenge | 2 | 2 | 3 |
| 1 mg FDT (12) | 48 | 41 | 48 |
| 1 mg FDT (13) | 26 | 34 | 35 |
| 1 mg FDT (14) | N/A | N/A | 67 |
| Nicorette Microtab 2 mg | 4 | 4 | 5 |
| Nicotinell Mint Chewing gum (2 mg) | 0 | 0 | 5 |

N/A = Not applicable (not assessed)

As can be seen from table 13A-13C, formulations of the invention provided very high absorption, above 40% or even above 50%. Also, since FDT 1 and 2 are comparable, only that FDT 2 does not contain buffer, the effect of inclusion of the buffer may be observed. It is noted that FDT1 has a final absorption being significantly higher than FDT2, illustrating how inclusion of buffer increases the absorption of nicotine. Also, It is observed that the absorption of nicotine is more or less constant at times 10 seconds, 20 seconds, and 90 seconds, illustrating how the disintegration time (about 10 seconds for FDT 1) is the limiting factor, and that the time for release of nicotine after disintegration as well as the time for absorption of nicotine is negligible for the present compositions.

The tablets of the example 6 and 7 are highly suitable to obtain nicotine formulations for use in the alleviation of nicotine craving, the formulations comprising a content of nicotine and a content of a pH regulating agent, wherein the formulations provide a peak saliva concentration of nicotine of more than 0.3 mg/mL, such as more than 0.5, mg/mL and a peak saliva pH of more than 7.5 during the first 120 seconds upon oral administration.

Example 11

Evaluation of Fast Disintegrating Tablets—Burning

In general experiments have disclosed that nicotine fast disintegrating tablets according to the invention result in high absorption efficiency of nicotine into the blood stream for a fast disintegrating tablet user. With such fast integration, high pH-value combined with high nicotine concentration, only a minor part of the nicotine is swallowed by the user instead of entering the blood system, thereby resulting in fast craving relief.

When pH in the mouth is high, the nicotine is used in a very efficient way. However, too high pH in the saliva of the fast disintegrating tablet users may not be desirable, since the highly alkaline pH-value results in problems with irritation and burning of the sublingual tissue.

Consequently, the fast disintegrating tablets of the invention are indeed suitable in that they provide an efficient utilization of nicotine and at the same time are pleasant to the user, i.e. with clearly diminished unwanted side effects, hereunder particularly so called nicotine burning in the throat.

Evaluation of burning sensation is performed as described in the following.

Nicotine burning was evaluated by a test panel of 7 trained assessors. After calibration by means of chewing two standard nicotine containing chewing gum with "known" burning intensity, each assessor evaluates the burning sensation in the throat on a scale from 1 to 15, where 15 is the most intense burning. Each assessor evaluates all samples twice. The evaluations are noted for the time periods indicated. Average values are calculated.

TABLE 14

Sensory evaluation

| | Time [seconds] | | |
|---|---|---|---|
| | 145 | 295 | 505 |
| | Burning score (1-15) | | |
| FDT (12) | 3.5 | 1.8 | 0.8 |
| FDT (14) | 6.6 | 4.5 | 2.7 |
| Nicotinell Mint Chewing gum (2 mg) | 4.6 | 4.6 | 3.4 |
| Nicotinell Mint Lozenge (2 mg) | 4.8 | 4.9 | 4.2 |
| Nicorette Microtab 2 mg | 6.4 | 5.9 | 5.5 |

Example 12—Alleviation of Nicotine Craving

Nicotine craving alleviation was tested using a panel of three users evaluating all samples twice. Each user noted the time from oral administration until craving relief, i.e. feeling the effect of nicotine reaching the head. The average times for FDT (12) and FDT (14) and three commercially available products are indicated in table 10.

TABLE 15

| Time before alleviation | FDT (12) | FDT (14) | Nicotinell Mint Chewing gum (2 mg) | Nicotinell Mint Lozenge (2 mg) | Nicorette Microtab (2 mg) |
|---|---|---|---|---|---|
| Average | 240 | 300 | 560 | 480 | 400 |

As can be seen from table 15, significantly faster alleviation was obtained compared to the commercially available products.

The invention claimed is:

1. An orally disintegrating nicotine tablet for alleviation of nicotine craving, the tablet comprising a content of nicotine and a content of a pH regulating agent,
wherein the tablet provides a peak saliva concentration of nicotine of more than 0.3 mg/mL and a peak saliva pH of more than 7.5 during the first 120 seconds upon oral administration,
wherein the tablet comprises at least one polyol in an amount of more than 40% by weight of the tablet,
wherein the tablet is configured to disintegrate within three minutes from oral administration, and
wherein the tablet comprises nicotine in an amount of at least 0.5 mg.

2. The orally disintegrating nicotine tablet according to claim 1, wherein the tablet provides a peak saliva concentration of nicotine of more than 0.5 mg/mL during the first 120 seconds upon oral administration.

3. The orally disintegrating nicotine tablet according to claim 1, wherein the tablet comprises said pH regulating agent in an amount of at least 0.5% by weight of the tablet.

4. The orally disintegrating nicotine tablet according to claim 1, wherein the pH regulating agent is selected from the group consisting of carbonates glycerinate, phosphate, glycerophosphate, acetate, glyconate or citrate of an alkali metal, ammonium, tris buffer, amino acids and mixtures thereof.

5. The orally disintegrating nicotine tablet according to claim 4, wherein the carbonates comprise monocarbonate, bicarbonate, sesquicarbonate, or a combination thereof.

6. The orally disintegrating nicotine tablet according to claim 1, wherein the tablet provides a peak saliva concentration of nicotine of more than 0.3 mg/mL and a peak saliva pH of more than 8 during the first 90 seconds upon oral administration.

7. The orally disintegrating nicotine tablet according to claim 1, wherein the tablet comprises microcrystalline cellulose in an amount of 1-10% by weight of the tablet.

8. The orally disintegrating nicotine tablet according to claim 1, wherein the tablet after administering to the oral cavity generates saliva, and at least a portion of said saliva is contained in the oral cavity in a period of at least 15 seconds prior to swallowing or spitting.

9. The orally disintegrating nicotine tablet according to claim 1, wherein said nicotine is provided as a nicotine salt.

10. The orally disintegrating nicotine tablet according to claim 9, wherein the nicotine salt is selected from nicotine ascorbate, nicotine aspartate, nicotine benzoate, nicotine monotartrate, nicotine bitartrate, nicotine chloride, nicotine citrate, nicotine fumarate, nicotine gensitate, nicotine lactate, nicotine mucate, nicotine laurate, nicotine levulinate, nicotine malate nicotine perchlorate, nicotine pyruvate, nicotine salicylate, nicotine sorbate, nicotine succinate, nicotine zinc chloride, nicotine sulfate, nicotine tosylate and hydrates thereof.

11. The orally disintegrating nicotine tablet according to claim 9, wherein the nicotine salt comprises nicotine bitartrate.

12. The orally disintegrating nicotine tablet according to claim 1, wherein said nicotine is provided as a complex between nicotine and an ion exchange resin, wherein said complex between nicotine and the ion exchange resin is nicotine polacrilex resin (NPR).

13. The orally disintegrating nicotine tablet according to claim 1, wherein the tablet is designed to disintegrate within a period of less than 60 seconds upon oral administration.

14. The orally disintegrating nicotine tablet according to claim 1, wherein said tablet further comprises a disintegrant in an amount of 1-10% by weight of the tablet.

15. The orally disintegrating nicotine tablet according to claim 14, wherein the disintegrant comprises cross-linked polyvinylpyrrolidone.

16. The orally disintegrating nicotine tablet according to claim 15, wherein at least 50% by weight of the cross-linked polyvinylpyrrolidone has a particle size below 50 micrometers.

17. The orally disintegrating nicotine tablet according to claim 15, wherein at least 25% by weight of the cross-linked polyvinylpyrrolidone has a particle size below 15 micrometers.

18. The orally disintegrating nicotine tablet according to claim 1, wherein the tablet has a weight of 25 to 200 mg.

19. A method of alleviation of nicotine craving by administering an effective amount of an oral nicotine formulation in the form of the tablet according to claim 1.

20. An oral nicotine pouch for alleviation of nicotine craving, the oral nicotine pouch comprising a powder formulation provided in a pouch, the formulation comprising a content of nicotine and a content of a pH regulating agent,
wherein the formulation provides a peak saliva concentration of nicotine of more than 0.3 mg/mL and a peak saliva pH of more than 7.5 during the first 120 seconds upon oral administration,
wherein the formulation comprises at least one polyol in an amount of more than 40% by weight of the formulation,
wherein the formulation is configured to disintegrate within three minutes from oral administration, and
wherein the pouch comprises nicotine in an amount of at least 0.5 mg.

21. The oral nicotine pouch according to claim 20, wherein the pouch comprises said powdered formulation in an amount of 100 to 800 mg.

* * * * *